(12) United States Patent
Antony

(10) Patent No.: US 9,610,311 B2
(45) Date of Patent: Apr. 4, 2017

(54) MEDICINAL COMPOSITION OF AMARANTH EXTRACT HAVING ENRICHED NITRATE CONTENT AND A METHOD OF PREPARING THE SAME

(71) Applicant: ARJUNA NATURAL EXTRACTS, LTD., Alwaye (IN)

(72) Inventor: Benny Antony, Ankamaly (IN)

(73) Assignee: ARJUNA NATURAL EXTRACTS, LTD., Alwaye (IN)

( * ) Notice: Subject to any disclaimer, the term of this patent is extended or adjusted under 35 U.S.C. 154(b) by 0 days.

(21) Appl. No.: 14/975,251

(22) Filed: Dec. 18, 2015

(65) Prior Publication Data
US 2016/0101138 A1    Apr. 14, 2016

Related U.S. Application Data

(63) Continuation of application No. PCT/IN2014/000430, filed on Jun. 26, 2014.

(30) Foreign Application Priority Data

Jun. 28, 2013  (IN) .......................... 2861/CHE/2013

(51) Int. Cl.
| | | |
|---|---|---|
| *A01N 65/00* | (2009.01) | |
| *A61K 36/21* | (2006.01) | |
| *A61K 9/00* | (2006.01) | |
| *A61K 9/68* | (2006.01) | |
| *A61K 36/185* | (2006.01) | |

(52) U.S. Cl.
CPC ............ *A61K 36/21* (2013.01); *A61K 9/0056* (2013.01); *A61K 9/0058* (2013.01); *A61K 9/0095* (2013.01); *A61K 36/185* (2013.01); *A61K 2236/00* (2013.01)

(58) Field of Classification Search
CPC .................................................... A61K 36/00
USPC ........................................................ 424/725
See application file for complete search history.

(56) References Cited

U.S. PATENT DOCUMENTS

| | | | |
|---|---|---|---|
| 7,777,074 B2 | 8/2010 | Kramer | |
| 8,034,836 B2 | 10/2011 | Kramer | |
| 8,048,921 B2 | 11/2011 | Kramer | |
| 8,178,572 B2 | 5/2012 | Kramer | |
| 8,183,288 B2 | 5/2012 | Kramer | |
| 8,298,589 B1 | 10/2012 | Bryan | |
| 8,303,995 B1 | 11/2012 | Bryan | |
| 8,435,570 B1 | 5/2013 | Bryan | |
| 8,455,531 B2 | 6/2013 | Kramer | |
| 8,466,187 B2 | 6/2013 | Kramer | |
| 8,569,368 B2 | 10/2013 | Kramer | |
| 8,569,369 B2 | 10/2013 | Kramer | |
| 8,952,045 B1 | 2/2015 | Kramer | |
| 8,952,046 B1 | 2/2015 | Kramer | |
| 8,952,047 B1 | 2/2015 | Kramer | |
| 8,957,100 B1 | 2/2015 | Kramer | |
| 8,957,101 B1 | 2/2015 | Kramer | |
| 9,180,140 B2 | 11/2015 | Lundberg | |
| 2012/0321724 A1 | 12/2012 | Bryan | |
| 2013/0071371 A1 | 3/2013 | Bryan | |
| 2013/0071494 A1 | 3/2013 | Bryan | |
| 2015/0352147 A1 | 12/2015 | Lundberg | |

FOREIGN PATENT DOCUMENTS

WO    WO 2010/035253 A1    4/2010

OTHER PUBLICATIONS

Larsen, FJ, Weitzberg, E, Lundberg, JO, Ekblom, B, Effects of dietary nitrate on oxygen cost during exercise, Acta Physiol, 191: 59-66 (2007).
Ashok Kumar. BS. Lakshman. K. Jayaveera. KN. Nandeesh. R. Manoj. B. and Ranganayakulu. D. Comparative in Vitro Anthelmintic activity of Three plants from the *Amaranthaccae* family, Arch. Biol. Sci.. Belulade. 62 (1).185-189 (2010).
Maiyo. ZC. Ngure. RM. Matasyoh. JC. and Chepkorir. R. Phytochemical constituents and Antimicrobial activity of Leaf Extracts of three *Amaranthus* plant species. African Journal of Biotechnology. 9(21):3178-3182 (2010). Academic Journals.
Antara, C. Evaluation of Physiochemical and Phytochemical parameters of Amaranthus Spinosus leaves. International Research Journal of Pharmacy. 3 (10):210-211 (2012).
Tsuchiya, K. Kanematsu. Y. Yoshizumi. M. Ohnishi. H. Kirima. K. Izawa.Y. Shikishima. M. Ishida. T. Kondo. S. and Kagami. S . Takiguchi. Y and Tamaki.T. Nitrite is an alternative source of NO in vivo. Am J Physiol Heart Circ Physiol 288:H2163-H2170 (2005). American Physiological Society.
Umar. KJ. Hassan. LG. Dangoggo. SM. Maigandi. SA. and Sani. NA. Nutritional and Anti-nutritional profile of spiny Amaranth (*Amaranthus viridis* Linn). Studia Universitatis "Vasile Goldis", Seria Stiintele Vietii. 21(4): 727-737 (2011).
Srivastava. R. Nutritional Quality of Some Cultivated and Wild species of *Amaranthus* L., International Journal of Pharmaceutical Sciences and Research. 2(12):3152-3156 (2011).
Akubugwo. IE. Obasi. NA. Chinyere. GC and Ugbogu. AE. Nutritional and chemical value of *Amaranthus hybridus* L. leaves from Afikpo. Nigeria. African Journal of Biotechnology. 6(24):2833-2839 (2007).
Soetan. KO. Aiyelaagbe. OO. The need for bioactivity-safety evaluation and conservation of medicinal plants—A review. Journal of Medicinal Plants Research. 3(5):324-328 (2009).

(Continued)

*Primary Examiner* — Michael Meller

(57) ABSTRACT

An extract of Amaranth, having enriched nitrate content, L-arginine, Flavonoids, saponins, alkaloids, carbohydrates, proteins, potassium, and with negligible amount of oxalic acid or oxalate content. The extract of Amaranth can be prepared from fresh or dried leaves and stem of Amaranth. Dosage forms of extract include fast melt tablet, lozenge, candy, chewing gum, beverage, tablet, capsule, pill, and powder. The extract of Amaranth enhances nitric oxide concentration, enhances nitrate level concentration, and enhances nitrite level in blood as well as in saliva. Administering the extract can lower blood pressure, increase physical endurance, increase swimming endurance, increase running endurance, and improve sexual performance among human beings.

4 Claims, 15 Drawing Sheets

(56) References Cited

OTHER PUBLICATIONS

Prakash, D. Pal. M, Nutritional and Antinutritional composition of vegetable and grain Amaranth leaves. Journal of the Science of Food and Agriculture. 57(4):573-583 (1991).
Bharadwaj. K. Murty. AS. An Investigation of Edible Plants for Soluble Oxalates and Calcium Oxalate Crystals. Bulletin of Medico-Ethno-Botanical Research. XII(3-4):153-156 (1991).
International search report for PCT/IN2014/000430 dated Nov. 12, 2014.
Noonan. SC. Savage. GP. Oxalate content of foods and its effect on humans. Asia Pacific J Clin Nutr 8(1):64-74 (1999).
Arslan. A., Uzun. M. Does the lower Nitric Oxide level cause cardiovascular changes in major depressed Women? European Review for Medical and Pharmacological Sciences. 12:309-313 (2008).
Mnkeni, AP. Masika. P. Maphaha.M. Nutritional Quality of Vegetable and Seed from different accessions of Amaranthus in South Africa. Water SA. 33(3)(Special Edition):377-380 (2007).
Oloyede. FM. Oloyede. FA. Obuotor E. M. Effect of Plant Maturity on the Antioxidant Profile of *Amaranthus cruentus* L. and *Celosia argentea* L.. Bull. Env. Pharmacol. Life Sci. 2(2):18- 21 (Jan. 2013).
Ahmed. SA. Hanif. S. Iftkhar. T. Phytochemical Profiling with Antioxidant and Antimicrobial Screening of *Amaranthus viridis* L. Leaf and Seed Extracts. Open Journal of Medical Microbiology. 3:164-171 (2013).
Kenjale. AA. Ham. KL. Stabler. T. Robbins. JL. Johnson. JL. VanBruggen, M. Privette. G. Yim. E. Kraus. WE. Allen. JD. Dietary Nitrate Supplementation Enhances Exercise Performance in Peripheral Arterial Disease. J Appl Physiol.110:1582-1591 (2011).
Ignarro. LJ. Fukuto. JM. Griscavage. JM. Rogers. NE. Byrns. RE, Oxidation of Nitric oxide in Aqueous Solution to Nitrite but not Nitrate: Comparison with Enzymatically formed Nitric oxide from L-arginine. Proc. Natl. Acad. Sci. USA. 90:8103-8107 (1993).
Ogbadoyi. EO. Musa. A. Oladiran. JA. Ezenwa. MIS. Akanya. FH. Effect of Processing methods on Some Nutrients. Antinutrients and Toxic Substances in Amaranthus Cruentus. International Journal of Applied Biology and Pharmaceutical Technology. 2(2):487-502 (2011).
Mou. B. Evaluation of Oxalate Concentration in the U.S. Spinach Germplasm Collection. Hort Science 43(6):1690-1693(2008).
European Food Safety Authority. Nitrate in vegetables Scientific Opinion of the Panel on Contaminants in the Food chain. Opinion of the Scientific panel on contaminants in the food chain pn a request from the European Commission to perform a scientific risk assessment in nitrate in vegetables. The EFSA Journal. 689:1-79 (2008).

| RAW MATERIAL/ EXTRACT | % OF EXTRACT | NITRATE (%) | OXALIC ACID (%) | SAPONINS (%) | ALKALOIDS (%) | CARBO-HYDRATE (%) | PROTEIN (%) | FLAVO-NOIDS (%) | L-ARGININE (%) | POTASSIUM (%) |
|---|---|---|---|---|---|---|---|---|---|---|
| AMARANTH LEAVES | NA | 1.5g/kg OF LEAVES | 1g/100g OF LEAVES | 1.68mg/100g OF LEAVES | 3.54mg/100g OF LEAVES | 5.5g/100g OF LEAVES | 5g/100g OF LEAVES | 0.83mg/100g OF LEAVES | 3.94g/100g PROTEIN | 54.2mg/100g OF LEAVES |
| FRESH LEAVES 100kg | NA | 150g (0.15%) | 1kg (1%) | 1.68g (0.00168%) | 3.54g (0.00354%) | 5.5kg (5.5%) | 5kg (5%) | 0.83g (0.00083%) | 197g (0.197%) | 54.2g (0.0542%) |
| METHANOL EXTRACT FROM FRESH LEAVES [EG.1] | 2 | 1.5 | 40 | 0.08 | 0.18 | 15 | 10 | 0.04 | 0.75 | 1.2 |
| WATER EXTRACT OF FRESH LEAVES [EG.2] | 3 | 1.6 | 35 | 0.09 | 0.25 | 16.5 | 15 | 0.05 | 0.94 | 1.5 |
| METHANOL EXTRACT OF DRIED LEAVES [EG.3] | 24 | 1.65 | 11 | 0.01 | 0.15 | 19.5 | 17.8 | 0.003 | 0.82 | 1.8 |
| WATER EXTRACT OF DRIED LEAVES [EG.4] | 25 | 1.7 | 10.5 | 0.02 | 0.01 | 18.3 | 16.6 | 0.004 | 0.66 | 1.95 |
| AMARANTH JUICE [EG.13] | 37.5 | 0.1 | 30 | 0.09 | 0.21 | 13.2 | 20 | 0.06 | 0.1 | 0.15 |
| PECTINASE TREATED WATER EXTRACT OF FRESH LEAVES OF AMARANTH [EG.5] | 3.5 | 2 | 30.2 | 2.3 | 1.2 | 20.5 | 18.6 | 1.5 | 1.6 | 2.3 |
| OXALIC ACID FREE AMARANTH EXTRACT [EG.6] | 2.2 | 5 | 0.09 | 3.1 | 1.8 | 20.8 | 19.4 | 2.1 | 1.8 | 4.5 |

*Fig. 14A*

| RAW MATERIAL/ EXTRACT | % OF EXTRACT | NITRATE (%) | OXALIC ACID (%) | SAPONINS (%) | ALKALOIDS (%) | CARBO-HYDRATE (%) | PROTEIN (%) | FLAVO-NOIDS (%) | L-ARGININE (%) | POTASSIUM (%) |
|---|---|---|---|---|---|---|---|---|---|---|
| AMARANTH LEAVES | NA | 1.5g/kg OF LEAVES | 1g/100g OF LEAVES | 1.68mg/100g OF LEAVES | 3.54mg/100g OF LEAVES | 5.5g/100g OF LEAVES | 5g/100g OF LEAVES | 0.83mg/100g OF LEAVES | 3.94g/100g PROTEIN | 54.2mg/100g OF LEAVES |
| ENRICHED EXTRACT OF AMARANTH BY EXTRACTION WITH HEXANE [EG.7] | 1.6 | 18 | 0.09 | 8 | 4 | 24 | 22 | 6 | 3 | 17 |
| ENRICHED EXTRACT OF AMARANTH BY EXTRACTION WITH CHLOROFORM [EG.8] | 1.6 | 16 | 0.07 | 9 | 5.1 | 26 | 21 | 5.3 | 4 | 15 |
| ENRICHED EXTRACT OF AMARANTH BY EXTRACTION WITH ETHYLENE DICHLORIDE [EG.9] | 1.6 | 17 | 0.08 | 7 | 4.3 | 23 | 22 | 6.9 | 6 | 16 |
| AMARANTH EXTRACT ENRICHED WITH AMLA EXTRACT [EG.11] | NA | 17 | 0.08 | 8.2 | 3.6 | 22.7 | 20.9 | 5.5 | 2.7 | 17 |
| PREPARATION OF FAST DISSOLVING 200-mg TABLETS [EG.21] | 40 | 7.2 | 0.04 | 3.2 | 1.6 | 9.6 | 8.8 | 2.4 | 1.2 | 6.8 |
| PREPARATION OF FAST DISSOLVING 1250mg TABLETS [EG.22] | 40 | 7.2 | 0.04 | 3.2 | 1.6 | 9.6 | 8.8 | 2.4 | 1.2 | 6.8 |

*Fig. 14B*

MEDICINAL COMPOSITION OF AMARANTH EXTRACT HAVING ENRICHED NITRATE CONTENT AND A METHOD OF PREPARING THE SAME

This application is a continuation of PCT International Application Serial Number PCT/IN2014/000430, filed Jun. 26, 2014, which claims priority of Indian Provisional Application No. filed 2861/CHE/2013, filed Jun. 28, 2013, all of which are incorporated by reference.

BACKGROUND

Nitric oxide is an important cellular signaling molecule involved in many physiological and pathological processes. It is a powerful vasodilator with a short half-life of a few seconds in the blood. Nitric Oxide is a free form of gas produced by the cells in our body. It is produced when enzymes in the body break down the amino acid Arginine, and is mainly used for intra-cellular communication. Nitric Oxide is required for key physiological functions within our body. It travels freely from one cell to another assisting in a variety of biological functions. Depending on the requirement, Nitric Oxide can act as a hormone, a neurotransmitter and an intracellular messenger.

Nitric Oxide is crucial for a variety of body functions, and it is essential that the cells produce adequate amount of this gas within our bodies. Body builders or those who perform rigorous physical activities need a higher amount of NO, as it allows for an increase in blood flow while building muscles. Signs of NO deficiency include extreme fatigue and physical weakness. It is useful in treating a variety of conditions such as insomnia, obesity, diabetes and sexual problems. In the cardiovascular system, NO is an important determinant of basal vascular tone, prevents platelet activation, limits leukocyte adhesion to the endothelium, and regulates myocardial contractility. NO may also play a role in the pathogenesis of common cardiovascular disorders, including hypotension accompanying shock states, essential hypertension, and atherosclerosis. Nitric oxide regulates blood circulation throughout the body, increases the diameter of blood vessels and prevents formation of clots. It assists the endothelial cells in controlling and relaxing blood vessels. Nitric oxide is a cytotoxic agent of macrophages, a messenger molecule of neurons, and a vasodilator produced by endothelial cells. The Immune cells within our body release Nitric Oxide to destroy bacteria, virus and other harmful foreign organisms that can cause infections. NO is also known to prevent tumour and cancerous growths within the body cells.

Nitric Oxide has been shown to be mediator of erectile function. Nitric Oxide stimulates, invigorates and amplifies the sexual response mechanism within the body. Sensory and mental stimulation causes the nerve cells to release nitric oxide. This causes the penis muscles to relax, allowing blood to flow into the penis and create an erection. The process remains the same for women too, as blood flow increases in their vaginal tissues. Nitric Oxide increases the endurance level of the muscle cells, enabling you to lift heavier load and perform strenuous activities with ease. Nitric Oxide acts as an intracellular messenger between various cells in the body, including the nerve cells. With adequate amount of NO present in the body, the communication between nerve cells is faster, leading to quick responses and an increase in focus and vigilance. Common disorders that promote atherosclerosis, such as hypertension, hyperlipidemia, smoking, and diabetes, are all associated with abnormal endothelial function, one manifestation of which is a comparative deficiency of bioactive NO. A deficiency of NO producing neurons in the gastrointestinal tract is believed to be responsible for certain abnormalities in gastrointestinal motility, such as Hirschsprung's disease, achalasia, and chronic intestinal pseudo-obstruction. NO is also believed to play an important role in gastric cytoprotection, possibly by way of increased mucosal blood flow and the modulation of gastric epithelial function.

Production of Nitric Oxide in Human Body (Biosynthesis)

NO is produced from the amino acid L-arginine by the enzymatic action of nitric oxide synthase (NOS). There are two endothelial forms of NOS: constitutive NOS (cNOS; type III) and inducible NOS (iNOS; type II). Co-factors for NOS include oxygen, NADPH, tetrahydrobiopterin and flavin adenine nucleotides. In addition to endothelial NOS, there is a neural NOS (nNOS; type I) that serves as a transmitter in the brain and in different nerves of the peripheral nervous system, such as non-adrenergic, non-cholinergic autonomic nerves that innervate penile erectile tissues and other specialized tissues in the body to produce vasodilation.

Under normal, basal condition in blood vessels, NO is continually being produced by cNOS. The activity of cNOS is calcium and calmodulin-dependent. There are two basic pathways for the stimulation of cNOS, both of which involve release of calcium ions from subsarcolemmal storage sites. First, shearing forces acting on the vascular endothelium generated by blood flow causes a release of calcium and subsequent cNOS activation. Therefore, increases in blood flow stimulate NO formation (flow-dependent NO formation). Second, endothelial receptors for a variety of ligands stimulate calcium release and subsequent NO production (receptor-stimulated NO formation). Included are receptors for acetylcholine, bradykinin, substance-P, adenosine, and many others vasoactive substances.

The other isoform of endothelial NOS is iNOS. It differs, in part, from cNOS in that its activation is calcium independent. Under normal, basal conditions, the activity of iNOS is very low. The activity of iNOS is stimulated during inflammation by bacterial endotoxins (e.g., lipopolysaccharide) and cytokines such as tumor necrosis factor (TNF) and interleukins. During inflammation, the amount of NO produced by iNOS may be a 1,000-fold greater than that produced by cNOS.

Production of NO from Dietary Nitrates

Dietary nitrate is an important source of nitric oxide in mammals. Green, leafy vegetables, and some root vegetables (such as beetroot) have high concentrations of nitrate. When eaten and absorbed into the bloodstream nitrate is concentrated in saliva (about 10 fold) and is reduced to nitrite on the surface of the tongue by a biofilm of commensal facultative anaerobic bacteria. This nitrite is swallowed and reacts with acid and reducing substances in the stomach (such as ascorbate) to produce high concentrations of nitric oxide.

An Acceptable Daily Intake (ADI) for nitrate of 3.7 mg/kg b.w./day, equivalent to 222 mg nitrate per day for a 60 kg adult was established by the former Scientific Committee on Food (SCF) and was reconfirmed by the Joint FAO/WHO Expert Committee on Food Additives (JECFA).

The bioactivation of nitrate from dietary or endogenous sources requires its initial reduction to nitrite, and because mammals lack specific and effective nitrate reductase enzymes, this conversion is mainly carried out by commensal bacteria in the gastrointestinal tract and on body surfaces. Nitrite is unique to the nitrogen oxides in its redox position between oxidative ($NO_2$ radical) and reductive (NO radical) signalling and its relative stability in blood and tissue. Once nitrite is formed, there are numerous pathways in the body for its further reduction to NO, involving haemoglobin, myoglobin, xanthine oxidoreductase, ascorbate, polyphenols and protons. The generation of NO by these pathways is greatly enhanced during hypoxia and acidosis, thereby ensuring NO production in situations for which the oxygen-dependent NOS enzyme activities are compromised. Dietary nitrate is rapidly absorbed in the upper gastrointestinal tract. In the blood, it mixes with the nitrate formed from the oxidation of endogenous NO produced from the NOS enzymes. After a meal rich in nitrate, the levels in plasma increase greatly and remain high for a prolonged period of time.

Once in the oral cavity, commensal facultative anaerobic bacteria use nitrate as an alternative electron acceptor to oxygen during respiration, effectively reducing salivary nitrate to nitrite by the action of nitrate reductases. Human nitrate reduction requires the presence of these bacteria—suggesting a functional symbiosis relationship—as mammalian cells cannot effectively metabolize this anion. The salivary nitrate levels can approach 10 mM and nitrite levels 1-2 mM after a dietary nitrate load. When saliva enters the acidic stomach (1-1.5 1 per day), much of the nitrite is rapidly protonated to form nitrous acid ($HNO_2$; pKa ~3.3), which decomposes further to form NO and other nitrogen oxides. Nitrite reduction to NO is greatly enhanced by reducing compounds such as vitamin C and polyphenols, both of which are abundant in the diet.

The percentage of nitrate content in leafy vegetables is very less to significantly increase the nitric oxide level in the blood when taken orally. A larger quantity is required to be ingested at regular interval to get significant level of nitric oxide in the blood. Consumption of large quantity of leafy vegetables on regular basis is not convenient in such a busy life. Thus, providing a supplement developed from nitrate containing plant in the form of compact delivery system will be a convenient alternate to generate higher nitric oxide content in the blood. Moreover, as nitrates are required to be converted into nitrites in the mouth itself (by commensal facultative anaerobic bacteria), it will be more advantageous if the nitrate rich formulation can be delivered to oral cavity in the form of chewing gum, lozenge, candy etc. Delivery via oral cavity offers certain advantages over conventional delivery of drugs.

The sites of drug administration in the oral cavity include the floor of the mouth (sublingual), the inside of the cheeks (buccal) and the gums (gingival). Drug administration via oral cavity offers several distinct advantages:

The buccal mucosa is relatively permeable with a rich blood supply, robust in comparison to the other mucosal tissues.

Bypass the first-pass effect and non-exposure of the drugs to the gastrointestinal fluids.

Improve the performance of many drugs, as they are having prolonged contact time with the mucosa.

High patient acceptance compared to other non-oral routes of drug administration.

As a result of adhesion and intimate contact, the formulation stays longer at the delivery site improving API bioavailability using lower API concentrations for disease treatment.

Harsh environmental factors that exist in oral delivery of a drug are circumvented by buccal drug delivery.

A lot of work has been done for enhancing the level of nitric oxide in the blood for human beings and method of administration of medicaments/formulations, including those originated from plants (botanical source) available in nature in plenty. A short review of some of the prior art will elucidate how we have addressed the issue compared to other prior art and how effectively we could address enhancing the level of nitric oxide in the blood for human beings and the method of treating diseases as well as source for overcoming certain deficiencies of humanbeings.

U.S. Pat. No. 8,303,995, Bryan et al, discloses a nitrite formulations and their use as nitric oxide prodrugs. The Compositions comprising from about 40 weight parts to about 1000 weight parts of a botanical nitrate source; from about 20 weight parts to about 500 weight parts of a botanical source of nitrite reduction activity; and from about 4 weight parts to about 100 weight parts of a nitrite salt.

The botanical source of nitrite reduction activity is selected from the group consisting of hawthorn berry, Schisandra, green tea, beet root, pine bark, holy basil, gymnema sylvestre, ashwagandha root, salvia, St. John wort, broccoli, stevia, spinach, gingko, kelp, tribulus, eleuthero, epimedium, eucommia, rhodiola, green tea, codonopsys, panax ginseng, astragalus, dodder seed, cordyceps, berries, tea, beer, grapes, wine, olive oil, chocolate, cocoa, coffee, walnuts, peanuts, borojo, pomegranates, popcorn, yerba mate, and mixtures thereof. Methods of reducing triglycerides or reducing C-reactive protein levels are also provided.

U.S. Pat. No. 8,298,589, Bryan et al, is related to 'Nitrite formulations and their use as nitric oxide prodrugs having a composition comprising nitrite salt (10 mg to 100 mg), nitrate salt (50 mg to 500 mg), ascorbic acid (100 mg to 2000 mg) of sodium and potassium.

Patent publication No US 20130071494, Bryan et al, also discloses a nitrite formulations and their use as nitric oxide prodrugs. The compositions comprise of from about 40 weight parts to about 1000 weight parts of a botanical nitrate source; from about 20 weight parts to about 500 weight parts of a botanical source of nitrite reduction activity; and from about 4 weight parts to about 100 weight parts of a nitrite salt Use of said composition in methods of reducing triglycerides or reducing C-reactive protein levels are also disclosed here.

Patent publication No US 20120321724, and WO 201323217 Bryan et al, discloses a method of measuring in vivo nitric oxide and nitrite levels in individuals by providing a salivary nitrite test substrate, testing salivary nitrite levels with the test substrate, measuring nitrite levels detected in the testing; and correlating the measured nitrite levels with in vivo nitric oxide bio-availability.

In patent No. U.S. Pat. No. 8,435,570, Bryan et al, disclose a composition comprising a nitrite salt, a nitrate salt, and ascorbic acid. A method of enhancing cardiovascular performance or treating adverse cardiovascular event in a mammal is also provided.

Patent publication No 20130071371, Bryan et al, is related to a composition and method of providing nitric oxide and nitrite therapy to patients whereby a therapeutic amount including a dispersable medium is bioavailable within approximately 30 minutes of administration including. In embodiments of the disclosure, nitric oxide is produced in the oral cavity.

In the above patents, the nitrate source is either synthetic one or from a botanical nitrate source which includes spinach, beet root, artichoke, holybasil, green tea etc.

Supplementation of Amaranth extract enriched with nitrate enhances the nitrate and nitrite levels in the body.

Presence of vitamin C promotes the conversion of nitrite to nitric oxide in body thereby increasing the antioxidant potential in body.

The formulation of nitrate enriched Amaranth extract with Vitamin C in the present formulation further improves the generation of nitric oxide by promoting the conversion of nitrite delivered from Amaranth extract to nitric oxide in the body. Vitamin C used may be of synthetic or natural origin.

*Amaranthus* are dietary leafy vegetables belonging to the family Amaranthaceae. Amaranth belongs to the genus *Amaranthus* and various species include *Amaranthus dubius, Amaranthus spinosus, Amaranthus fimbriatus, Amaranthus floridanus, Amaranthus graecizans* etc. Other dietary sources of nitrate are Spinach (*Spinacia oleracia*, family: Amaranthaceae), beet root (*Beta vulgaris*, family: Amaranthaceae), lettuce (*Lactuca sativa*, family: Asteraceae) etc.

The genus *amaranthus* contains approximately 70 species of worldwide distribution including pigweeds, water hemps, and grain *amaranthus*. For human consumption there are cultivated grain amaranths—*A. caudatus, A. cruentus* and *A. hypochondriacus* and vegetable amaranths—mainly *A. dubius, A. tricolor* and *A. cruentus*. Nowadays, the grain *amaranthus* are cultivated from the temperate to tropical zone and the vegetable amaranths mainly in the South Africa and South Asia.

These plants, which grow 90 centimeters to 150 centimeters tall, are abundant weeds in many parts of the world. All amaranth have alternate simple leaves. They may have some red color present on the stems. They bear minute, greenish flowers in dense clusters at the top of the plants. Their seeds may be brown or black in weedy species and light-colored in domestic species. Some amaranth species have been grown as a grain crop and a garden vegetable in various parts of the world, especially in South America.

*Amaranthus* are very promising crops. The main reasons could be content of protein, fat and active substances. The content of seed protein is in the range 13-18% with very good balanced amino acids. The lysine content is relatively high in the comparison with common cereals. The content of crude proteins in leaves is from 27 to 49% in d.m. what is more than in the leaves in the spinach. *Amaranthus* have comparable or higher amounts of essential amino acids as whole egg protein. The fat content is in the range 0.8-8.0%. The linoleic acid is the predominant fatty acid, with lesser amount of oleic and palmitic acids.

SUMMARY

Disclosure provides a medicinal composition obtained from the extract of Amaranth. Disclosure provides an extract of Amaranth having low oxalic acid content. The Amaranth extract includes
- about 0.1% to about 20% nitrates;
- about 0.1% to about 10% of L-arginine;
- about 0.001% to about 10% of flavonoids;
- about 0.01% to about 15% of saponins;
- about 0.01% to about 10% of alkaloids;
- about 10% to about 30% of carbohydrates;
- about 5% to about 25% of proteins;
- about 5% to about 25% potassium; and,
- about 0.01% to about 50% of total oxalic acid. Determination of total oxalic acid content included measurement of free oxalic acid and oxalates in the extract.

The disclosure also provides oral dosage forms of the composition of Amaranth such as fast melt tablets, lozenge, chewing gum etc to make it convenient for buccal absorption. The disclosure also provides dosage forms such as tablets, capsules, pills, powders etc for absorption from the stomach.

The disclosure provides methods for producing the Amaranth extract. The extract of Amaranth can be prepared from fresh or from dried leaves and stem of Amaranth.

Some embodiments of the composition are found to be useful for the enhancing the amount of nitric oxide in blood plasma. Some embodiments enhance the amount of nitric oxide in saliva. Some embodiments enhance the level of nitrate and nitrite in blood plasma. Some embodiments of the extract enhance the level of nitrate and nitrite in saliva. Some embodiments enhance the antioxidant activity in mammals. In some embodiments, the composition lowers blood pressure (hypertension). Some embodiments of the composition increase endurance.

In some embodiments, the Amaranth extract can be fortified by adding amla extract.

BRIEF DESCRIPTION OF THE DRAWINGS

FIG. 14 (Part A): Table showing the percentage of actives in different extract of Amaranth and fast dissolving tablets
FIG. 14 (Part B): Table showing the percentage of actives in different extract of Amaranth and fast dissolving tablets

DETAILED DESCRIPTION

Figure 1:
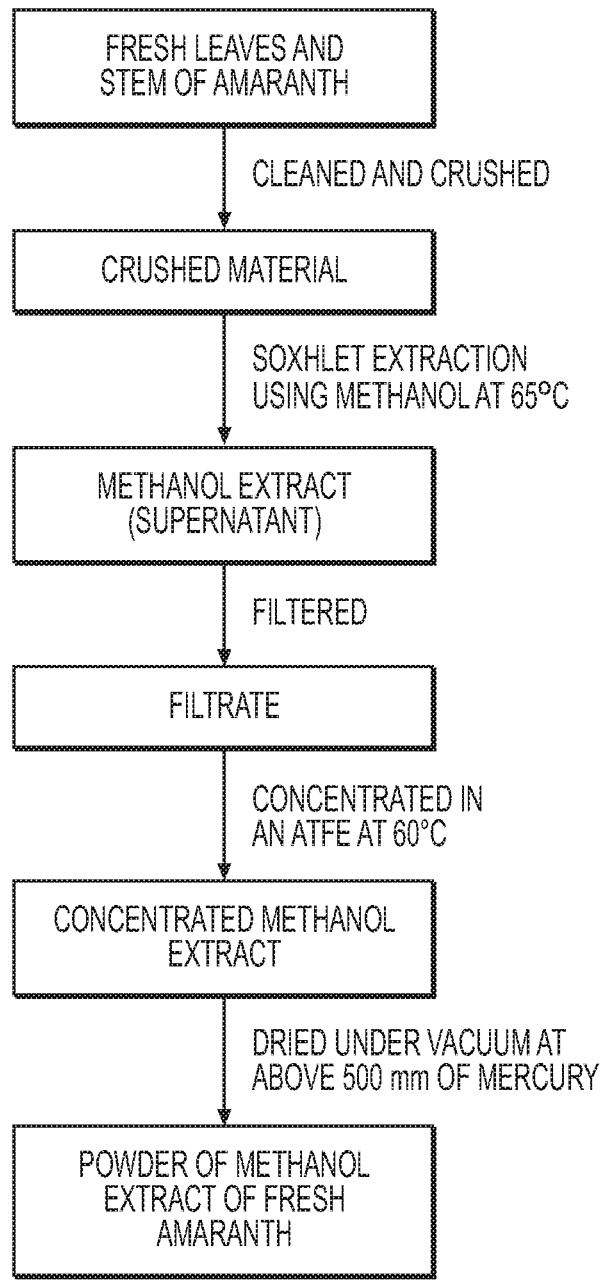
FIG. 1: Flow chart—Extraction of Fresh Amaranth with methanol.

The disclosure provides an entirely different medicinal composition prepared from Amaranth as nitrate source by a unique method of extraction. The disclosed processes provide an extract of Amaranth enriched with nitrate, L-arginine, flavonoids, carbohydrate, protein, saponins, alkaloids, potassium and having negligible oxalic acid or oxalate content. Many vegetables contain high amount of total oxalic acid in the form of free oxalic acid or oxalate salts and the oxalic or oxalate content is toxic to human health. The extracts from vegetables contain oxalic acid along with other active constituents. The extract of Amaranth also contains oxalic acid and oxalates. But in the disclosed methods, we removed the oxalic acid and oxalates from the Amaranth extract to provide an extract of Amaranth having negligible oxalic acid or oxalate content. The total oxalic acid content was measured by HPLC method and provides the total of both free oxalic acid and oxalate salts in the extract.

The composition obtained from the enriched extract of amaranth is useful for lowering the blood pressure (hypertension), enhancing the level of nitric oxide in the blood plasma and saliva, enhancing the level of nitrate and nitrite in blood plasma and saliva, enhance the antioxidant activity and increase the endurance. The disclosure relates to a medicinal composition of Amaranth extract. The composition has an enriched nitrate content, L-arginine, flavonoids, carbohydrate, protein, saponins, alkaloids, potassium and a negligible amount of oxalic acid or oxalate.

The Amaranth extract can be obtained from both fresh and dry leaves and stem of Amaranth. The extract when administered to mammals especially to human beings can lower the blood pressure (hypertension) and increase the endurance. If the same extract is further enriched by enzyme treatment it can enhance the capability of lowering the blood pressure (hypertension) and increasing the endurance.

It is further noted that the composition of enriched Amaranth extract origin has the property to enhance the amount of nitric oxide in blood plasma and saliva as well as the property to enhance the level of nitrate and nitrite in blood plasma and saliva. The composition is also found to be useful for enhancing the antioxidant activity.

Some embodiments provide a composition obtained from the extract of Amaranth from fresh leaves and stem of Amaranth comprising enriched nitrate content, L-Arginine, flavonoids, saponins, alkaloids, potassium and having negligible amount of oxalic acid or oxalate content wherein nitrates are present in the extract in a range of 3% to 20%, L-Arginine are present in the extract from 1% to 10%, flavonoids are present in the extract in a range of 1% and 10%, saponins are present in the range of 5% to 15%, alkaloids are present in the range of 3% to 10%. The extract also contains carbohydrate from 10% to 30%, potassium content from 5% to 25% and proteins are present in a range of 5% to 25%.

Some embodiments provide an extract of Amaranth having low total oxalic acid content. The extract includes:
   about 0.1% to about 20% nitrates;
   about 0.1% to about 10% of L-arginine; (0.1-2%; 0.1-6%; 0.1-10%)
   about 0.001% to about 10% of flavonoids;
   about 0.01% to about 15% of saponins;
   about 0.01% to about 10% of alkaloids; (0.01-5%)
   about 10% to about 30% of carbohydrates;
   about 5% to about 25% of proteins;
   about 5% to about 25% potassium; and,
   about 0.01% to about 50% of total oxalic acid. The total oxalic acid includes free oxalic acid and oxalate salts in the extract.

In some embodiments of the extract, nitrates ranges from about 0.1% to about 3%. In some embodiments of the extract, nitrates ranges from about 1% to about 10%. In some embodiments of the extract, nitrates ranges from about 10% to about 20%. In some embodiments of the extract, nitrates ranges from about 3% to about 20%. In some embodiments of the extract, L-arginine ranges from about 0.1% to about 2%. In some embodiments of the extract, L-arginine ranges from about 0.1% to about 6%. In some embodiments of the extract, L-arginine ranges from about 0.1% to about 10%. In some embodiments of the extract, alkaloids ranges from about 0.01% to about 5%. In some embodiments of the extract, total oxalic acid ranges from about 0.01% to about 0.1%. Total oxalic acid content in the extracts was determined by HPLC method to measure both free oxalic acid and oxalates content in the extracts. In some embodiments of the extract, total oxalic acid ranges from about 0.01% to about 1%. In some embodiments of the extract, total oxalic acid ranges from about 0.1% to about 1%. In some embodiments of the extract, total oxalic acid ranges from about 1% to about 10%. In some embodiments of the extract, total oxalic acid ranges from about 1% to about 20%. In some embodiments of the extract, total oxalic acid ranges from about 1% to about 30%. In some embodiments of the extract, total oxalic acid ranges from about 1% to about 40%. In some embodiments of the extract, total oxalic acid ranges from about 1% to about 50%. In some embodiments of the extract, total oxalic acid ranges from about 10% to about 20%.

Some embodiments provide an extract of Amaranth having low total oxalic acid content. The extract includes
   about 3% to about 20% nitrates;
   about 1% to about 10% of L-arginine;
   about 1% to about 10% of flavonoids;
   about 5% to about 15% of saponins;
   about 3% to about 10% of alkaloids;
   about 10% to about 30% of carbohydrates;
   about 5% to about 25% of proteins;
   about 1% to about 5% of potassium; and,
   about 0.1% total oxalic acid. Total oxalic acid was measured by HPLC method to determine free oxalic acid and oxalates in the extract.

The disclosure provides extracts having enriched nitrate, L-arginine, flavonoids, carbohydrate, protein, saponins, alkaloids, potassium and having negligible oxalic acid or oxalate content wherein the extracts may be obtained from red Amaranth or Spleen amaranth or red Spinach (*Amaranthus dubius*) or any related species of amaranth like *A. caudatus, A. cruentus, A. hypochondriacus, A. tricolor, A. blitum, A. viridus* etc.

The disclosure also describes delivery of the nitrate enriched formulations orally as fast melt tablets, lozenge, candy, chewing gum, beverage etc to make it convenient for absorption from the mouth and also in the form of tablets, capsules, pills, powders etc to be absorbed from the stomach. Some embodiments provide a dosage form having the Amaranth extract. The dosage form is selected from the group consisting of fast melt tablet, lozenge, candy, chewing gum, beverage, tablet, capsule, pill, and powder.

Some embodiments provide a method of lowering blood pressure by administering the extract of Amaranth. Some embodiments provide a method of enhancing nitric oxide concentration in blood following administration of the Amaranth extract. Some embodiments provide, a method of increasing physical endurance by administering an extract of Amaranth. Some embodiments provide a method for increasing swimming endurance by administering the Amaranth extract. Some embodiments provide a method for increasing running endurance by administering an Amaranth extract. Some embodiments provide a method for improving sexual performance by administering an Amaranth extract. Some embodiments provide a method of enhancing nitrate level in blood by administering an extract of Amaranth. Some embodiments provide a method of enhancing nitrite level in blood by administering an extract of Amaranth. Some embodiments provide a method of enhancing nitrate level in saliva by administering an extract of Amaranth. Some embodiments provide a method of enhancing nitrite level in saliva by administering an extract of Amaranth.

Some embodiments provide a method of enhancing nitric oxide level in saliva by administering an extract of Amaranth.

In some embodiments as shown in Example 26, administering fast dissolving tablet containing Amaranth extract enriched with nitrate, led to increased levels of $NO_3$, $NO_2$ and NO content in plasma compared to plasma levels prior to administration of tablet. In some embodiments, $NO_3$ level increases about 6 fold the baseline value after 1 hour. In some embodiments, $NO_2$ level increases more than 6 fold. In some embodiments, NO level increases by about 6 fold.

In some embodiments as shown in Example 27, administering fast dissolving tablet containing Amaranth extract enriched with nitrate, led to increased $NO_3$, $NO_2$ and NO levels in saliva when compared to baseline prior to administration of the tablet. In some embodiments, $NO_3$ level increases about 6.9 fold of the baseline value after 1 hour. In some embodiments, $NO_2$ level increases more than 9.2 fold. In some embodiments, NO level increases 7.5 fold.

In some embodiments as shown in Example 28, administering Amaranth extract enriched with nitrate mixed with water, led to increased levels of $NO_3$, $NO_2$ and NO level in saliva when compared to levels in saliva prior to administration of extract. In some embodiments, $NO_3$ level increases 6.6 fold the baseline value after 1 hour. In some embodiments, $NO_2$ level increases 9.1 fold. In some embodiments, NO level increases 7.3 fold.

In some embodiments, administration of Amaranth extract enhanced plasma level of nitrate by 2 fold to 10 fold. In some embodiment, administration of Amaranth extract enhanced plasma level of nitrite by about 3 fold to about 15 fold. In some embodiments, administration of Amaranth extract enhanced plasma level of nitric oxide by about 2 fold to about 10 fold.

In some embodiments, administration of Amaranth extract enhanced saliva level of nitrate by 2 fold to 10 fold. In some embodiment, administration of Amaranth extract enhanced saliva level of nitrite by about 3 fold to about 15 fold. In some embodiments, administration of Amaranth extract enhanced saliva level of nitric oxide by about 2 fold to about 10 fold.

In some embodiments, administering Amaranth extract enriched with nitrate enhanced the nitrate and nitrite levels in the body. It is likely that presence of vitamin C promotes the conversion of nitrite to nitric oxide in body thereby increasing the antioxidant potential in body. Some embodiments provide a formulation of nitrate enriched Amaranth extract with Vitamin C, wherein administering the formulation further improves the generation of nitric oxide by promoting the conversion of nitrite delivered from Amaranth extract to nitric oxide in the body. Vitamin C added to the Amaranth extract may be of synthetic or natural origin.

The disclosure provides different extracts of Amaranth extracted by using solvents like water, methanol, ethanol, isopropanol, n-butanol, methyl acetate, ethyl acetate, propyl acetate, n-butyl acetate and combinations thereof Low molecular weight alcohols that can be used in preparation of the extract include methanol, ethanol, isopropanol, n-butanol and combinations thereof. Esters that can be used for extract preparation include methyl acetate, ethyl acetate, propyl acetate, n-butyl acetate and combinations thereof. Alkanes that can be used for preparation of the extract include pentane, hexane, heptane, isooctane, and combinations thereof.

Various species of Amaranth from which extract can be prepared include, *Amaranthus acanthochiton, Amaranthus acutilobus, Amaranthus viridis, Amaranthus albus, Amaranthus arenicola, Amaranthus australis, Amaranthus bigelovii, Amaranthus blitoides, Amaranthus blitum, Amaranthus brownie, Amaranthus californicus, Amaranthus cannabinus, Amaranthus caudatus, Amaranthus chihuahuensis, Amaranthus chlorostachys, Amaranthus crassipes, Amaranthus crispus, Amaranthus cruentus, Amaranthus deflexus, Amaranthus dubius, Amaranthus fimbriatus, Amaranthus floridanus, Amaranthus graecizans, Amaranthus greggii, Amaranthus hybridus, Amaranthus hypochondriacus, Amaranthus leucocarpus, Amaranthus lineatus, Amaranthus lividus, Amaranthus mantegazzianus, Amaranthus minimus, Amaranthus muricatus, Amaranthus obcordatus, Amaranthus oleraceous, Amaranthus palmeri, Amaranthus paniculus, Amaranthus polygonoides, Amaranthus powellii, Amaranthus pringlei, Amaranthus pumilus, Amaranthus quitensis, Amaranthus retroflexus* etc.

In some embodiments, the extract of Amaranth includes a second extract. The second extract is selected from the group consisting of amla extract, turmeric extract, grape seed extract, green tea extract, pomegranate extract, cocoa extract, coconut root extract, rosemary extract, mint leaf extract, star anise, sweet basil extract, cinnamon extract/clove extract, ginger extract, cumin seed extract, black pepper extract, fenugreek extract, or combinations thereof.

In some embodiments of the extract of Amaranth, the Amaranth is selected from the group consisting of *Amaranthus caudatus, Amaranthus cruentus, Amaranthus tricolor, Amaranthus blitum, Amaranthus viridis, Amaranthus dubis* or combinations thereof.

Various methods for the preparation of the extract enriched with nitrate content, L-arginine, flavonoids, carbohydrate, protein, saponins, alkaloids, potassium and having negligible oxalic acid or oxalate content prepared by the extraction of fresh leaves of Amaranth are as under:

In some embodiments (refer FIG. 1), the fresh leaves and stem of Amaranth is cleaned, crushed and extracted for 5 hrs using methanol at 65° C. in a Soxhlet extractor and then filtered. The resultant extract is concentrated in an Agitated thin film evaporator (ATFE) at a temperature of 60° C. to form concentrated extract. Later the concentrated extract is dried under vacuum at above 500 mm of mercury to form powder of "methanol extract" of fresh Amaranth.

In some embodiments, a method of preparing a powdered extract of fresh Amaranth is provided. The method includes crushing fresh leaves and stem of Amaranth to obtain a crushed material. Then extracting the crushed material with methanol to obtain a supernatant and residue. Then filtering the supernatant to obtain a filtrate. Then concentrating the filtrate to obtained a concentrated filtrate. Then drying the concentrated filtrate to obtain the powdered extract of fresh Amaranth.

Figure 2:
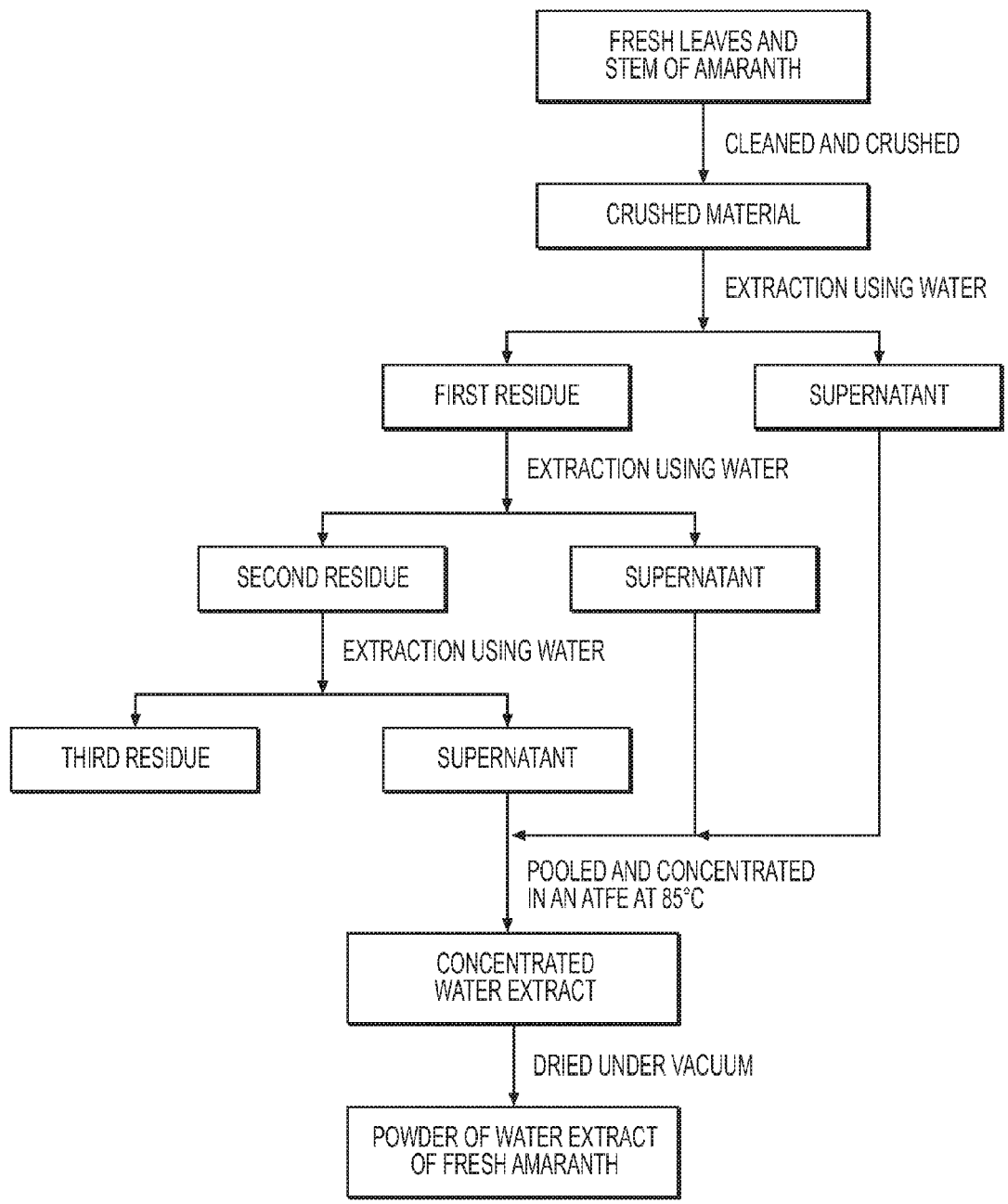
FIG. 2: Flow chart—Extraction of Fresh Amaranth with water.

According to another embodiment (refer FIG. 2), the fresh leaves and stem of Amaranth is cleaned, crushed and extracted for about 1 hr using water in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 85° C. to form concentrated extract. Later the concentrated extract is dried under vacuum at above 500 mm of mercury to form powder of "water extract" of fresh Amaranth.

Some embodiments provide a method of preparing a powdered extract of fresh Amaranth. The method includes crushing fresh leaves and stem of Amaranth to obtain a crushed material. Then extracting the crushed material with water to obtain a supernatant and a residue. Next, concentrating the supernatant to obtain a concentrated water extract. Then drying the concentrated water extract to obtain a powdered extract of fresh Amaranth.

Figure 3:
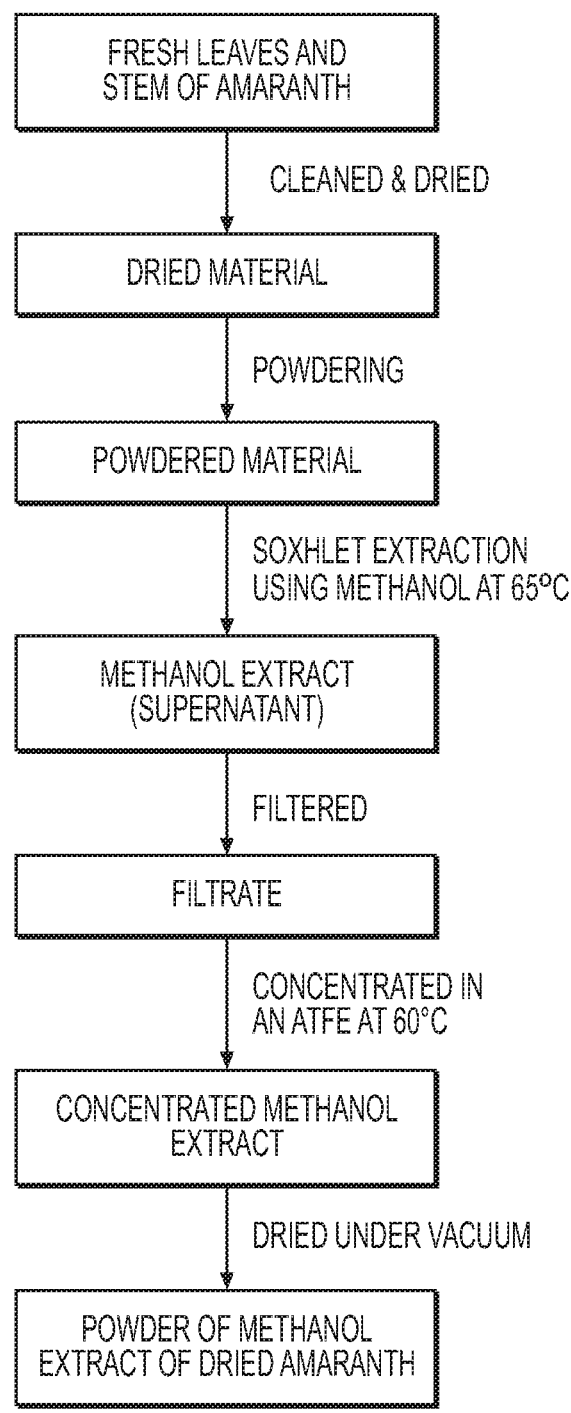
FIG. 3: Flow chart—Extraction of Dried Amaranth with methanol.

In some embodiments (refer to FIG. 3), the fresh leaves and stem of Amaranth is cleaned, dried and powdered. Then the powder is extracted for 5 hrs using methanol at 65° C. in a Soxhlet extractor and then filtered. The resultant extract is concentrated in an Agitated thin film evaporator (ATFE) at a temperature of 60° C. to form concentrated extract. Later the concentrated extract is dried under vacuum at above 500 mm of mercury to form powder of "methanol extract" of dried Amaranth.

Some embodiments provide a method of preparing a powdered extract of dried Amaranth. The method includes powdering dried leaves and stem of Amaranth to obtain a powdered material. Next, the powdered material is extracted with methanol to obtain a supernatant. Then the supernatant is filtered to obtain a filtrate. Next, concentrating the filtrate to obtain a concentrated methanol filtrate. Then drying the concentrated methanol filtrate to obtain the powdered extract of dried Amaranth.

Figure 4:
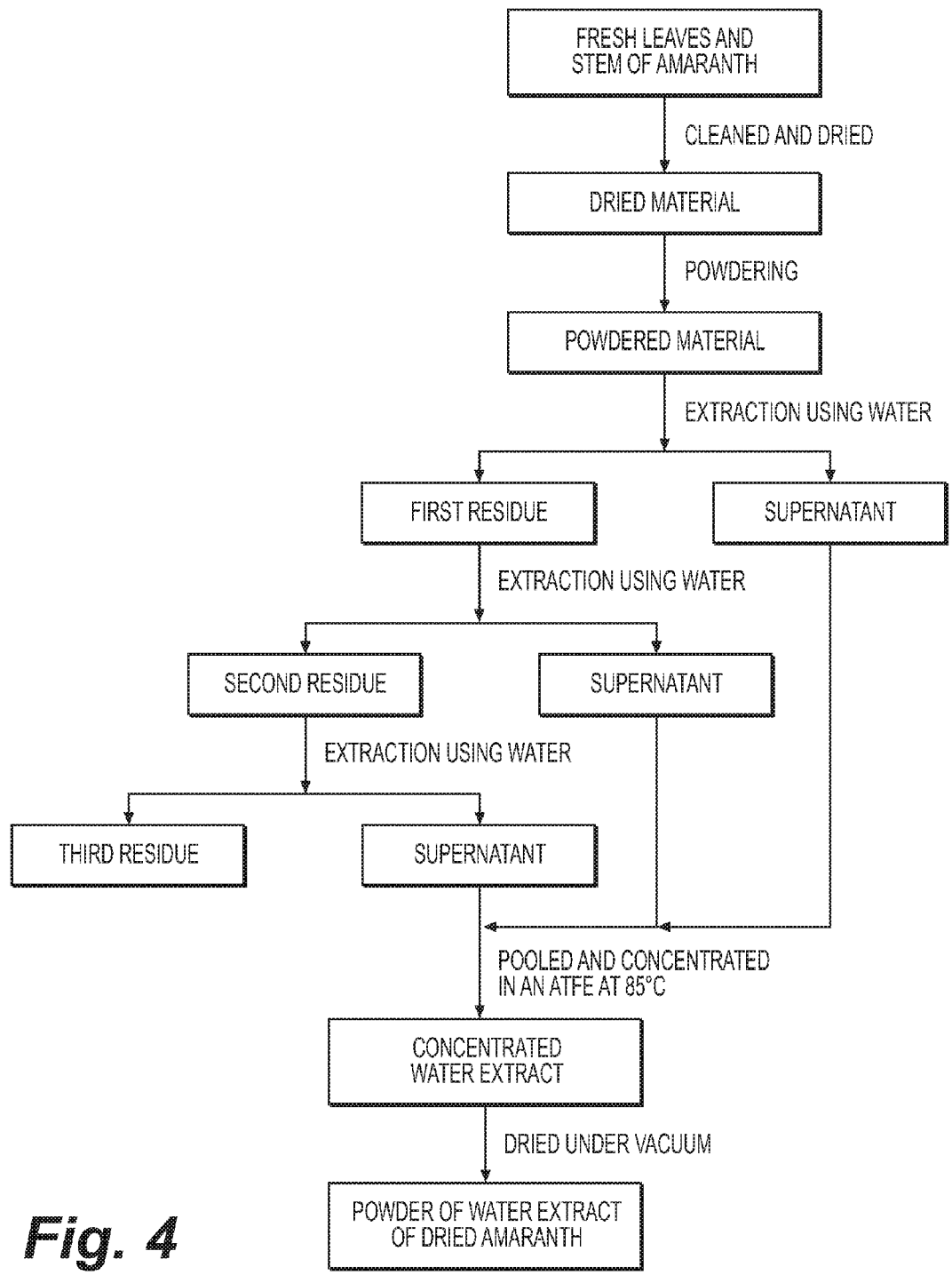
FIG. 4: Flow chart—Extraction of dried Amaranth with water.

According to another embodiment (refer to FIG. 4), the fresh leaves and stem of amaranth is cleaned, dried and powdered. The powder is extracted for about 1 hr using water in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 85° C. to form concentrated extract. Later the concentrated extract is dried under vacuum at above 500 mm of mercury to form powder of "water extract" of dried Amaranth.

Some embodiments provide a method of preparing a powdered extract of dried

Amaranth. The method includes powdering dried leaves and stem of Amaranth to obtain a powdered material. Then, the powdered material is extracted with water to obtain a supernatant and a residue. Next, the supernatant is concentrated to obtain a concentrated water extract. The concentrated water extract is dried to obtain a powdered extract of dried Amaranth.

Figure 5:
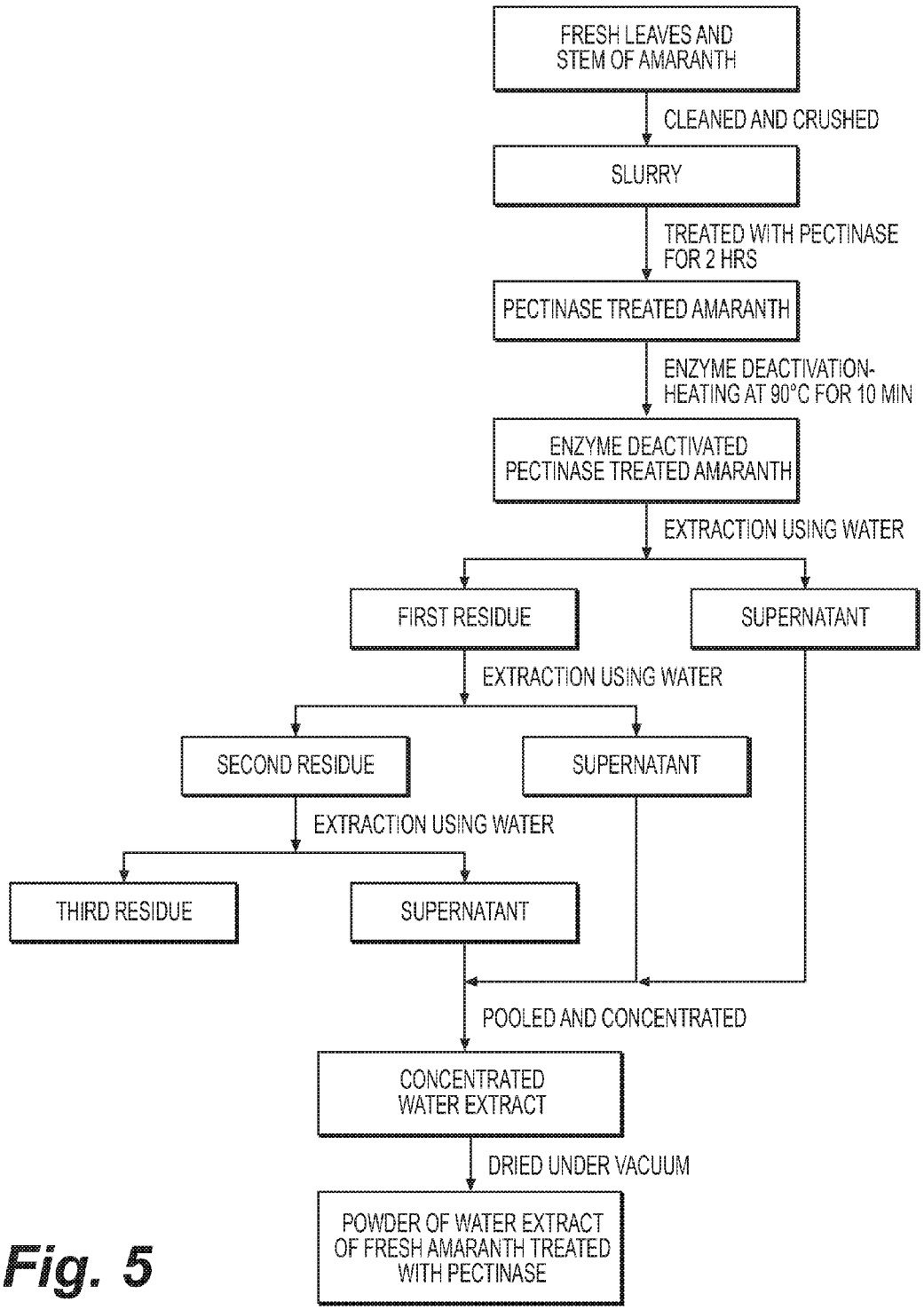
FIG. 5: Flow chart—Extraction of Fresh Amaranth by treating with pectinase.

In another embodiment (refer to FIG. 5), the fresh leaves and stem of amaranth is cleaned and crushed to form slurry. The slurry is a treated with pectinase (1%) for 2 hrs. Then the enzyme is deactivated by heating the slurry at 90° C. for 10 minutes. The pectinase treated amaranth slurry is extracted for about 1 hr using water in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 85° C. to form concentrated extract. Later the concentrated extract is dried under vacuum at above 500 mm of mercury to form powder of pectinase treated "water extract" of Amaranth.

In some embodiments of the method of preparing the Amaranth extract, the method includes crushing fresh leaves and stem of Amaranth to obtain a slurry. Then treating the slurry with pectinase to obtain a pectinase treated material. Then heating the pectinase treated material to obtain a pectinase-deactivated material. Next, extracting the pectinase-deactivated material with water to obtain a supernatant and a residue. Then, concentrating the supernatant to obtain a concentrated supernatant. And drying the concentrated supernatant to obtain a powdered extract of fresh Amaranth.

Figure 6:
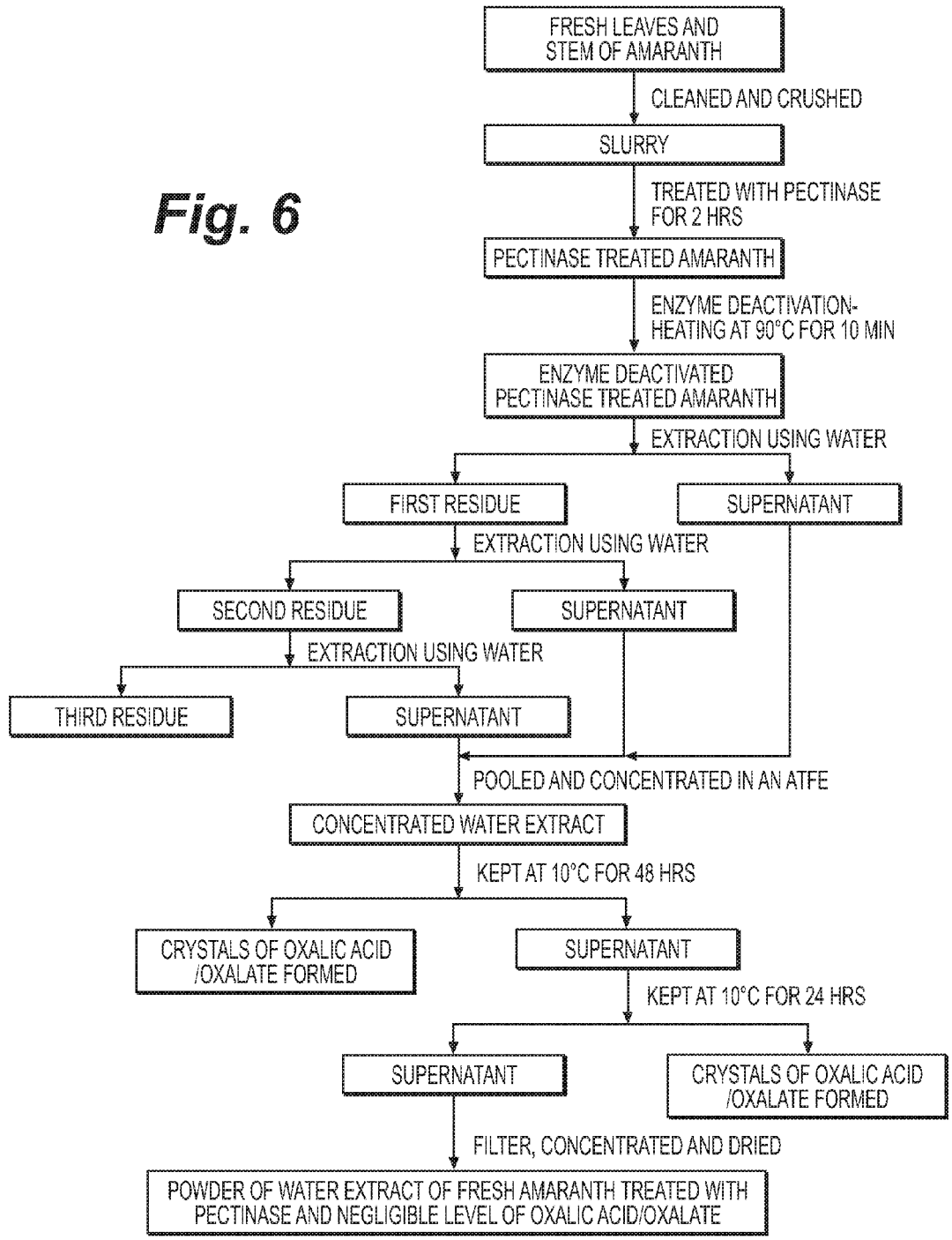
FIG. 6: Flow chart—Extraction of Fresh Amaranth by treating with pectinase and removal of Oxalic acid.

In yet another embodiment, (refer to FIG. 6), the fresh leaves and stem of Amaranth is cleaned and crushed to form slurry. The slurry is a treated with pectinase (1%) for 2 hrs. Then the enzyme is deactivated by heating the slurry at 90° C. for 10 minutes. The pectinase treated Amaranth slurry is extracted for about1 hr using water in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 85° C. to form concentrated extract. Keep the concentrated water extract at 10° C. for 48 hr to crystallize oxalic acid or oxalates. Decant the supernatant and again keep the supernatant at 10° C. for another 24 hr to crystallize remaining oxalic acid or oxalates. Decant and filter the supernatant and dry under vacuum at above 500 mm of mercury to get oxalic acid or oxalate free extract of Amaranth.

In some embodiments a method of preparing an extract of Amaranth is provided. The method includes crushing fresh leaves and stem of Amaranth to obtain a slurry, then treating the slurry with pectinase to obtain a pectinase treated material, followed by heating the pectinase treated material to obtain a pectinase-deactivated material. Next the pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid or oxalate and a second supernatant. The second supernatant is cooled at 10° C. for 24 hours to obtain a third supernatant and a second oxalic acid or oxalate crystals. Then the third supernatant is filtered to obtain a filtrate. Then the filtrate is concentrated to obtain a concentrated filtrate. And the concentrated filtrate is dried to obtain a powdered extract of Amaranth. In some embodiments, the powdered extract has less than 0.1% oxalic acid.

Figure 7:
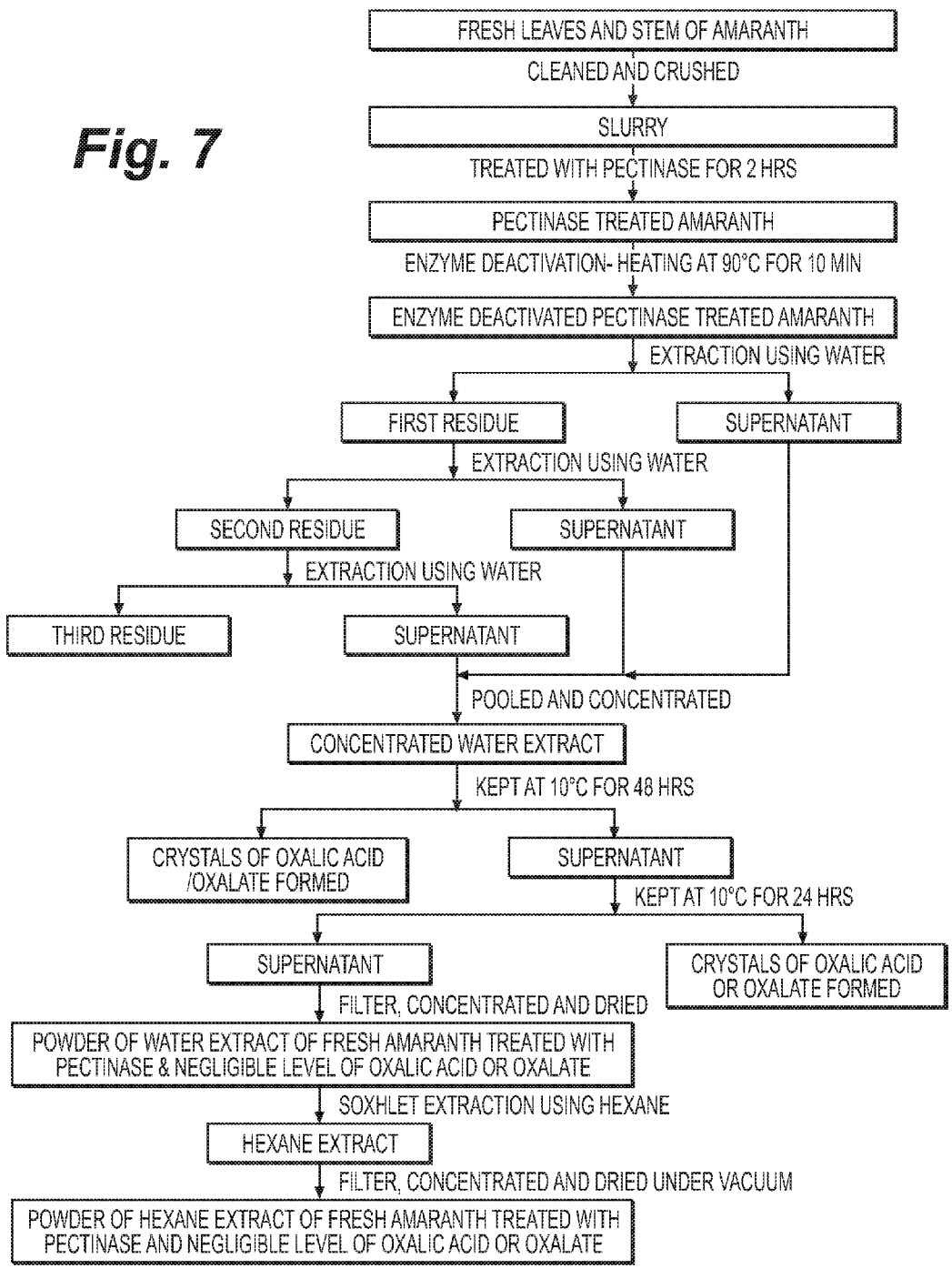
FIG. 7: Flow chart—Hexane Extract of Fresh Amaranth after treating with pectinase and removal of Oxalic acid.

In accordance with another embodiment (refer to FIG. 7) an Amaranth extract having enriched nitrate content is provided. A dried powder of oxalic acid or oxalate free extract of Amaranth is obtained after treating with pectinase and removal of oxalic acid is further extracted with hexane for 6 hours in a soxhlet extractor. Then filter and concentrate the hexane extract in an Agitated thin film evaporator (ATFE). The concentrated hexane extract is dried under vacuum to get powder of hexane extract of fresh Amaranth after treating with pectinase and removal of oxalic acid and having enriched nitrate content.

Some embodiments provide a method of preparing an extract of Amaranth having enriched nitrate content. The method includes crushing fresh leaves and stem of Amaranth to obtain a slurry. The slurry is treated with pectinase to obtain a pectinase treated material. Next, the pectinase treated material is heated to deactivate the pectinase and obtain a pectinase-deactivated material. Next, the pectinase-deactivated material is extracted with water to obtain a supernatant and a residue. Next, the supernatant is concentrated to obtain a concentrated water extract. The concentrated water extract is cooled at 10° C. for 48 hours and then filtered to obtain crystals of oxalic acid or oxalate and a second supernatant. The second supernatant is cooled at 10° C. for 24 hours to obtain a third supernatant and a second oxalic acid or oxalate crystals. The third supernatant is filtered to obtain a filtrate. The filtrate is concentrated to obtain a concentrated filtrate. The concentrated filtrate is dried to obtain a powdered extract. Next the powdered extract is treated with hexane to obtain a mixture. Then the mixture is filtered to obtain a filtrate. Then the filtrate is concentrated to obtain a concentrated hexane extract. Then the concentrated hexane extract is dried to obtain a powdered hexane extract.

Figure 8:
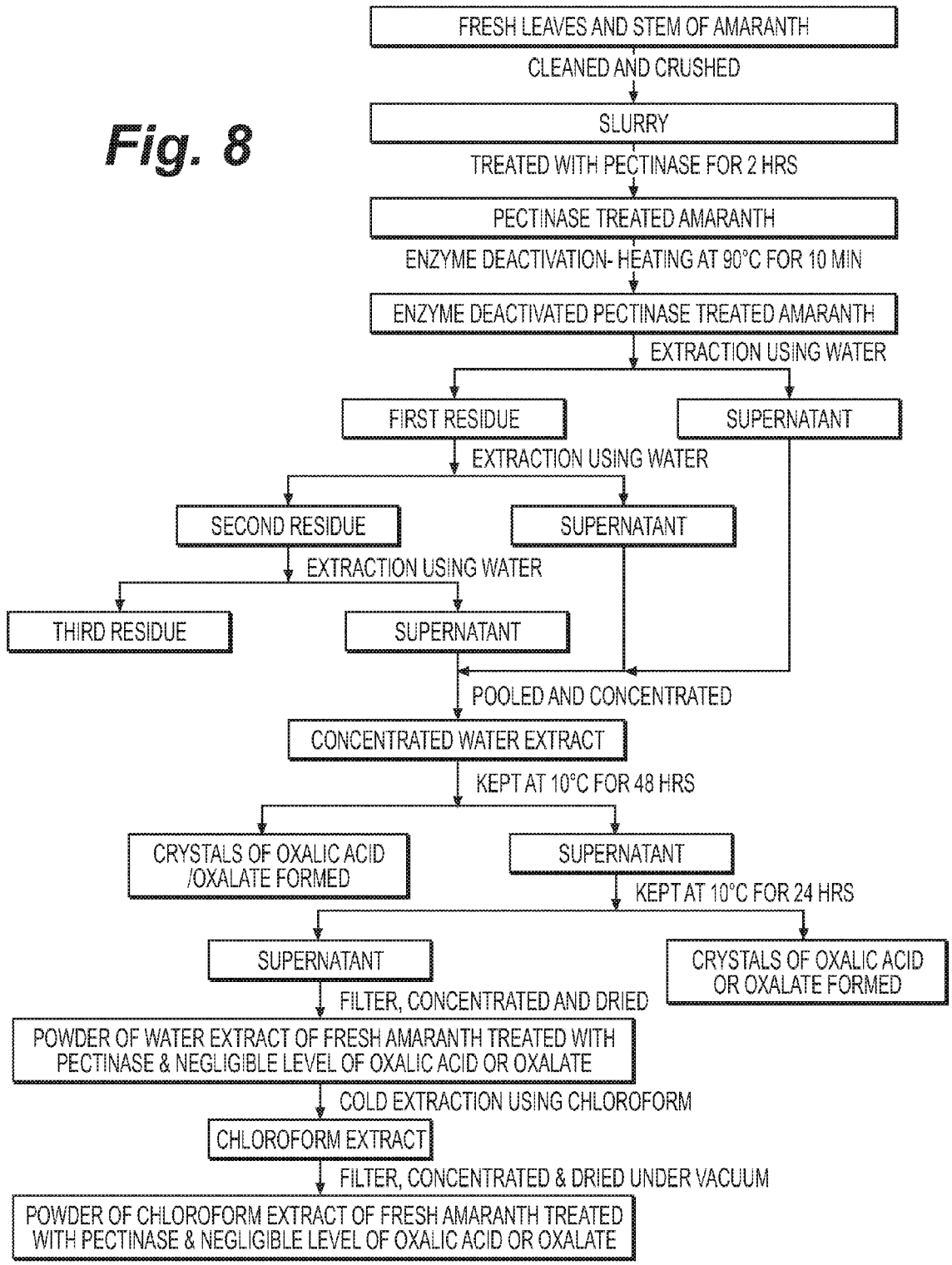
FIG. 8: Flow chart—Chloroform Extract of Fresh Amaranth after treating with pectinase and removal of Oxalic acid.

In another embodiment (refer FIG. 8), the dried powder of oxalic acid or oxalate free extract of Amaranth obtained after treating with pectinase and removal of oxalic acid is further extracted with chloroform by cold extraction instead of hexane. Filter and concentrate the chloroform extract in an Agitated thin film evaporator (ATFE). Then it is dried under vacuum to get powder of chloroform extract of fresh Amaranth after treating with pectinase and removal of oxalic acid.

Some embodiments provide a method of preparing an extract of Amaranth. The method includes crushing fresh leaves and stem of Amaranth to obtain a slurry. Then slurry is treated with pectinase to obtain a pectinase treated material. Then the pectinase treated material is heated to obtain a pectinase-deactivated material. Then the pectinase-deactivated material is extracted with water to obtain a supernatant and a residue. Then the supernatant is concentrated to obtain a concentrated water extract. Then the concentrated water extract is cooled at 10 C for 48 hours followed by filtering to obtain crystals of oxalic acid or oxalate and a second supernatant. Then the second supernatant is cooled at 10° C. for 24 hours to obtain a third supernatant and a second oxalic acid or oxalate crystals. Then the third supernatant is filtered to obtain a filtrate. Then the filtrate is concentrated to obtain a concentrated filtrate. Then the concentrated filtrate is dried to obtain a powdered extract. Then the powdered extract is treated with chloroform to obtain a mixture. The mixture is filtered to obtain a filtrate. The filtrate is concentrated to obtain a concentrated chloroform extract. The concentrated chloroform extract is dried to obtain a powdered chloroform extract.

Figure 9:
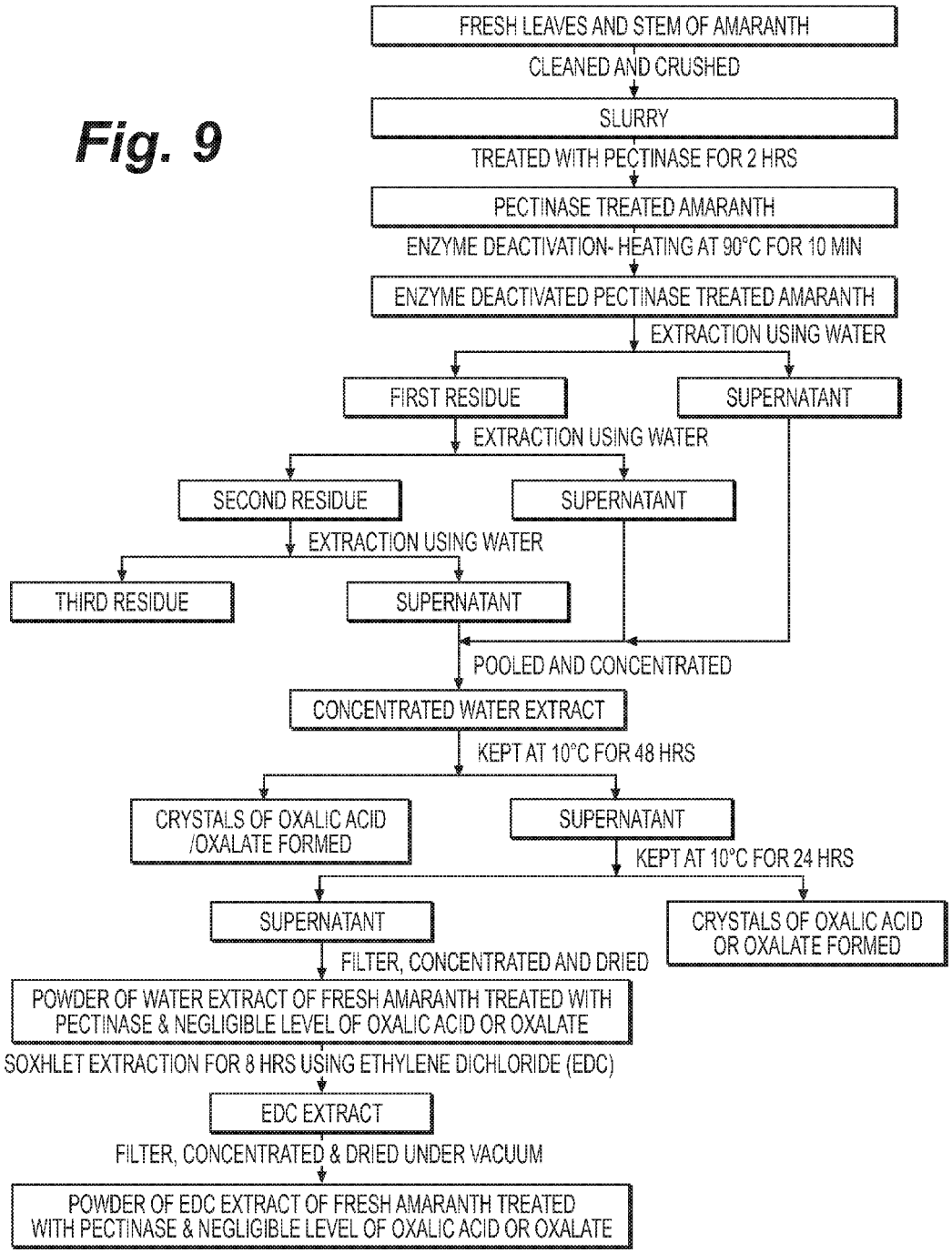
FIG. 9: Flow chart—EDC Extract of Fresh Amaranth after treating with pectinase and removal of Oxalic acid.

According to yet another embodiment (refer to FIG. 9), the dried powder of oxalic acid or oxalate free extract of Amaranth obtained after treating with pectinase and removal of oxalic acid is further extracted with ethylene dichloride (EDC) for 6 hours in a soxhlet extractor instead of Hexane/ Chloroform. Filter and concentrate the chloroform extract in an Agitated thin film evaporator (ATFE). Then it is dried under vacuum to get powder of chloroform extract of fresh Amaranth after treating with pectinase and removal of oxalic acid.

Some embodiments provide a method of preparing an extract of Amaranth. The method includes crushing fresh leaves and stem of Amaranth to obtain a slurry. The slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours followed by filtering to obtain crystals of oxalic acid or oxalate and a second supernatant. The second supernatant is cooled at 10° C. for 24 hours to obtain a third supernatant and a second set of crystals of oxalic acid or oxalate. The third supernatant is filtered to obtain a filtrate. The filtrate is concentrated to obtain a concentrated filtrate. The concentrated filtrate is dried to obtain a powdered extract. The powdered extract is dried with ethylene dichloride to obtain a mixture. The mixture is filtered to obtain a second filtrate. The second filtrate is concentrated to obtain a concentrated ethylene dichloride extract. The concentrated ethylene dichloride extract is dried to obtain a powdered ethylene dichloride extract.

Figure 11:
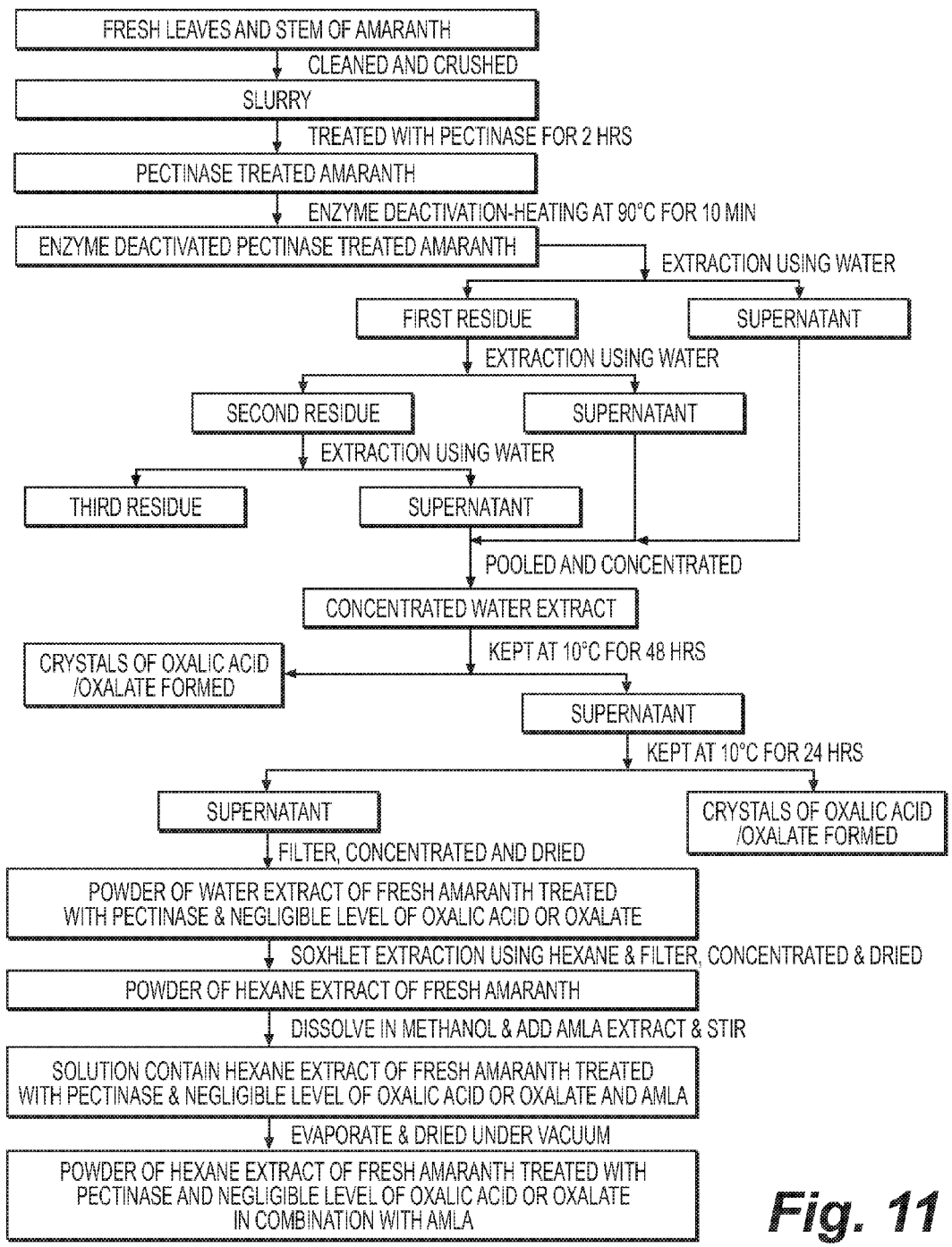
FIG. 11: Flow chart—Hexane Extract of Fresh Amaranth after treating with pectinase and removal of Oxalic acid in combination with Amla.

In another embodiment (refer to FIG. 11), the dried powder of oxalic acid or oxalate free extract of Amaranth obtained after treating with pectinase and removal of oxalic acid is further extracted with hexane for 6 hours in a soxhlet extractor. Then filter and concentrate the hexane extract in an Agitated thin film evaporator (ATFE). The concentrated hexane extract is dried under vacuum to get powder of hexane extract. It is dissolved in methanol and Amla extract already prepared is added and stirred for 1 hr at 100 rpm using mechanical stirrer. Evaporate and dry under vacuum to form powder. Thus a hexane extract of fresh Amaranth after treating with pectinase and removal of oxalic acid in combination with Amla is obtained.

Figure 10:
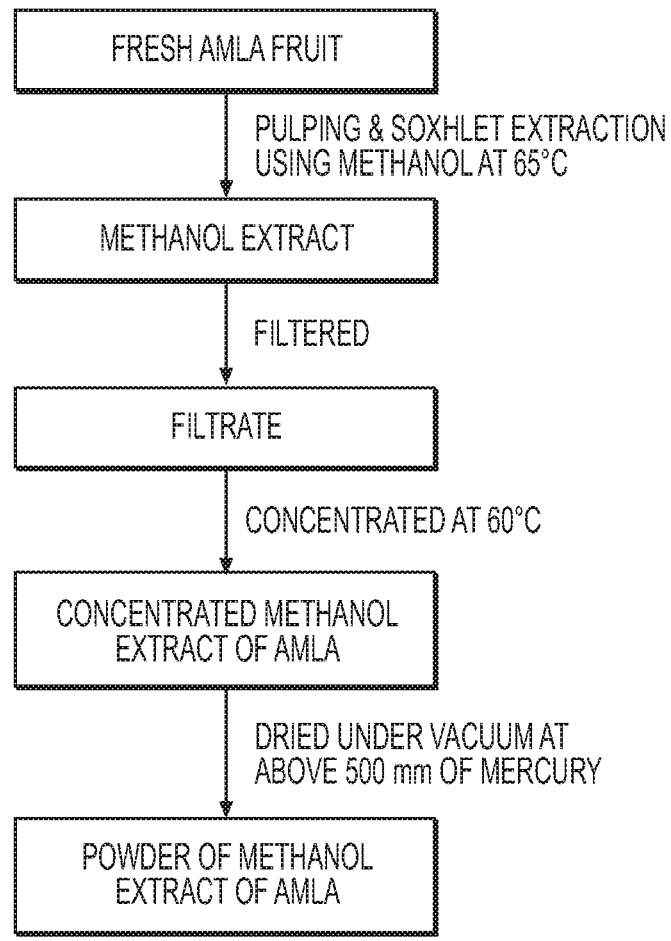
FIG. 10: Flow chart—Extraction of Amla.

The Amla extract (refer to FIG. 10) used here can be prepared according to the following method.

Pulp the fruits of amla and extract the pulp using methanol at 65° C. in a Soxhlet extractor for 5 hrs. The resultant methanol extract is filtered and concentrated in an Agitated thin film evaporator (ATFE) at a temperature of 60° C. to form concentrated extract. Dry the concentrated extract under vacuum at above 500 mm of mercury to form powder of methanol extract of Amla.

Some embodiments provide a method of preparing an extract of Amaranth. The method includes crushing fresh leaves and stem of Amaranth to obtain a slurry. Then the slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours followed by filtering to obtain crystals of oxalic acid or oxalate and a second supernatant. The second supernatant is cooled at 10° C. for 24 hours to obtain a third supernatant and a second oxalic acid or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a mixture. The mixture is filtered to obtain a second filtrate. The second filtrate is concentrated to obtain a concentrated hexane extract. The concentrated hexane extract is dried to obtain a powdered hexane extract. The powdered hexane extract is dissolved in methanol to obtain a solution of hexane extract of Amaranth. A powder of methanol extract of Amla is added to the solution of hexane extract of Amaranth to obtain a second mixture. The second mixture is evaporated to obtain an evaporate. The evaporate is dried to obtain a powder of Amaranth and Amla extract. The powdered methanol extract of Amla extract is prepared by a process including pulping fresh Amla (*Emblica officinalis*) fruit to obtain a pulp. The pulp is extracted with methanol to obtain a filtrate. The filtrate is concentrated to obtain a concentrated methanol extract of Amla. The concentrated methanol extract of Amla is dried to obtain the powdered methanol extract of Amla.

In some embodiments, amla extract/turmeric extract/ grape seed extract/green tea extract/pomegranate extract/ cocoa extract/coconut root extract/rosemary extract/mint leaf extract/star anise/sweet basil extract/cinnamon extract/ clove extract/ginger extract/cumin seed extract/black pepper extract/fenugreek extract are added to the pectinase treated fresh leaves of Amaranth having low total oxalic acid or oxalate content to fortify the Amaranth extract. The combination extracts can be administered to a mammal for enhancing the amount of nitric oxide in blood.

Figure 13:
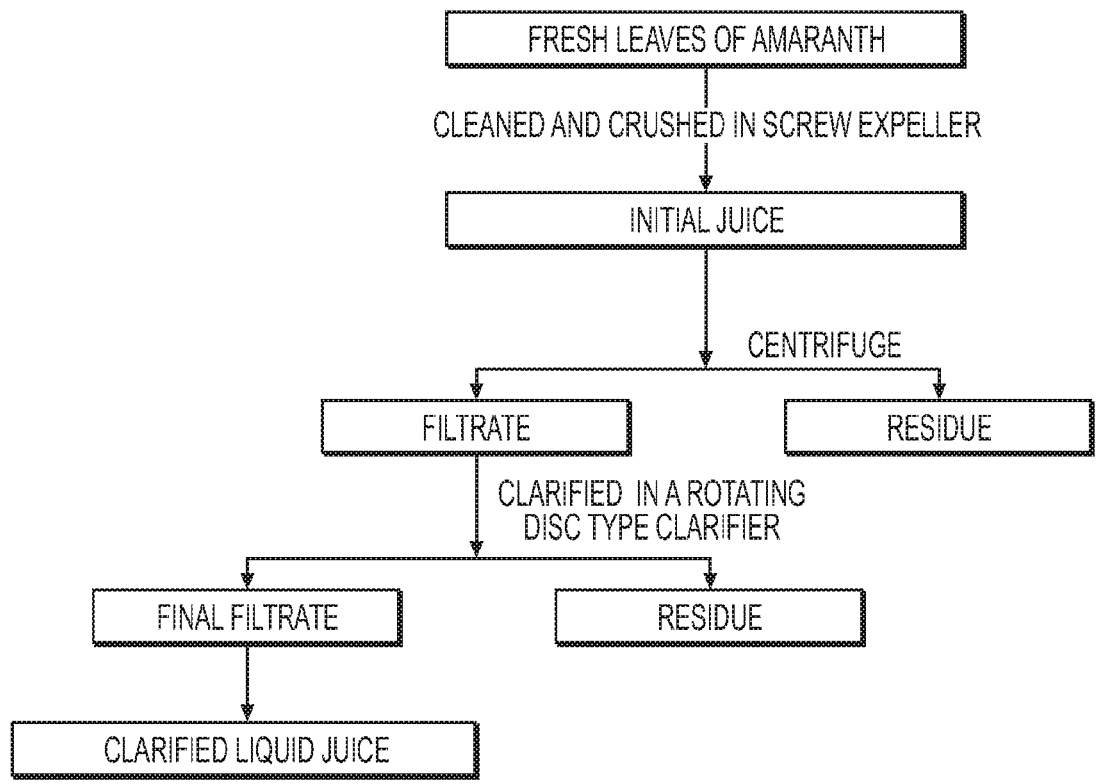
FIG. 13: Flow chart—Preparation of Amaranth Juice.

In some embodiments (refer to FIG. 13), the fresh leaves of amaranth is cleaned and crushed in the screw expeller. Initial Juice obtained on the tray of the screw expeller is collected in the feed tank under room temperature of 27° C. Initial juice is centrifuged to obtain filtrate and residue is removed. Filtrate is clarified in a rotating disc type clarifier (RPM—18000) to obtain final filtrate and residue. Residue is removed and final filtrate is collected (clarified liquid juice of leaves of Amaranth).

Details of some of the trials/experiments carried out and findings are explained below by way of examples.

EXAMPLE 1

Preparation of Amaranth Fresh Leaves Extract with Methanol.

Fresh Amaranth were collected (100 Kg). Leaves and stem of fresh Amaranth were cleaned and crushed. Crushed materials were filled in the Soxhlet extractor and extracted with methanol (300 L). The extraction was carried out for 5 hrs at a temperature of about 65° C. After the completion of extraction, the supernatant was filtered and concentrated in an Agitated thin film evaporator (ATFE) at a temperature of 60° C. to form concentrated methanol extract. Concentrated methanol extract was dried under vacuum at above 500 mm of mercury to get powder of methanol extract of fresh Amaranth (Yield 2 Kg). See also extract preparation in FIG. 1.

The nitrate content in methanol extract of fresh Amaranth by ion chromatography was found to be 1.5%.

EXAMPLE 2

Preparation of Amaranth Fresh Leaves Extract with Water.

Fresh Amaranth were collected (100 Kg). Leaves and stem of fresh Amaranth were cleaned and crushed. Water in an amount ten times the quantity of crushed material of Amaranth was added to form a mixture. The extraction was performed using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract. Concentrated water extract was dried under vacuum at above 500 mm of mercury to get powder of water extract of fresh Amaranth. (Yield 3%). See also extract preparation in FIG. 2.

The nitrate content in water extract of fresh Amaranth by ion chromatography was found to be 1.6%.

EXAMPLE 3

Preparation of Amaranth Dried Leaves Extract with Methanol.

Fresh Amaranth were collected (100 Kg). Leaves and stem of fresh Amaranth were cleaned and dried. Dried leaves and stem were powdered. Powdered Amaranth were filled in the Soxhlet apparatus and extracted with methanol (500 L). The extraction was carried out for 5 hrs at a temperature of about 65° C. After the completion of extraction, the supernatant was filtered and concentrated in an Agitated thin film evaporator (ATFE) at a temperature of 60° C. to form concentrated methanol extract. Concentrated methanol extract was dried under vacuum at above 500 mm of mercury to get powder of methanol extract of dried amaranth. When starting with 100 kg of fresh amaranth, a yield of 24 Kg of powder of methanol extract of dried amaranth was obtained. See also extract preparation in FIG. 3.

The nitrate content in methanol extract of dried Amaranth by ion chromatography was found to be 1.65%.

EXAMPLE 4

Preparation of Amaranth Dried Leaves Extract ith Water.

Fresh Amaranth were collected (100 Kg). Leaves and stem of fresh Amaranth were cleaned and dried. Dried Amaranth was powdered. Water in an amount ten times the quantity of powder of dried Amaranth was added to the powder of Amaranth to form a mixture. The extraction was performed using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract. Concentrated water extract was dried under vacuum at above 500 mm of mercury to get powder of water extract of dried Amaranth. (Yield 25%). See also extract preparation in FIG. 4.

The nitrate content in water extract of dried Amaranth by ion chromatography was found to be 1.7%.

EXAMPLE 5

Enhanced Yield of Amaranth Extract by Treatment with Pectinase.

Fresh Amaranth were collected (100 Kg). Leaves and stem of fresh Amaranth were cleaned and crushed to make slurry. The slurry was treated with pectinase (1%) for 2 Hrs. The enzyme was deactivated by heating the slurry at 90° C. for 10 minutes. After the enzyme treatment, the pectinase treated fresh leaves were extracted with water. The extraction was performed with water using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract. Concentrated water extract was dried under vacuum at above 500 mm of mercury to get powder of water extract of fresh Amaranth (Yield 3.5 Kg). See also extract preparation in FIG. 5.

Nitrate content of the extract was found to be 2% as determined by ion chromatography.

EXAMPLE 6

Oxalic Acid or Oxalates Free Amaranth Extract.

Fresh Amaranth were collected (100 Kg). Leaves and stem of fresh Amaranth were cleaned and crushed to make slurry. The slurry was treated with pectinase (1%) for 2 Hrs. The enzyme was deactivated by heating the slurry at 90° C. for 10 minutes. After the enzyme treatment, the pectinase treated fresh leaves were extracted with water. The extraction was performed with water using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract.

Concentrated water extract was kept at 10° C. for 48 hr to crystallize oxalic acid or oxalates. The supernatant was decanted off and again kept at 10° C. for 24 hr to crystallize remaining oxalic acid or oxalates. The supernatant from this solution was decanted, filtered and evaporated to dryness under vacuum to get oxalic acid or oxalate free Amaranth extract (2.2 Kg). See also extract preparation in FIG. 6

Nitrate content of the extract was found to be 5% as determined by ion chromatography.

EXAMPLE 7

Enrichment of Nitrates in Amaranth Extract by Extraction with Hexane.

Fresh Amaranth were collected (100 Kg). Leaves and stem of fresh Amaranth were cleaned and crushed to make slurry. The slurry was treated with pectinase (1%) for 2 Hrs. The enzyme was deactivated by heating the slurry at 90° C. for 10 minutes. The extraction was performed with water using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract.

Concentrated water extract was kept at 10° C. for 48 hr to crystallize oxalic acid or oxalates. The supernatant was decanted off and again kept at 10° C. for 24 hr to crystallize remaining oxalic acid or oxalates. The supernatant from this solution was decanted, filtered and evaporated to dryness under vacuum to get oxalic acid or oxalate free Amaranth extract (2.2 Kg).

This oxalic acid or oxalate free Amaranth extract was further extracted with hexane for 6 hours in a soxhlet extractor. The extract was filtered and evaporated to dryness under vacuum to get nitrate enriched Amaranth extract (1.6 Kg). Nitrate content of the extract was found to be 18% as determined by ion chromatography. See also extract preparation in FIG. 7.

EXAMPLE 8

Enrichment of Nitrates in Amaranth Extract by Extraction with Chloroform.

Fresh Amaranth were collected (100 Kg). Leaves and stem of fresh Amaranth were cleaned and crushed to make slurry. The slurry was treated with pectinase (1%) for 2 Hrs. The enzyme was deactivated by heating the slurry at 90° C. for 10 minutes. The extraction was performed with water using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract.

Concentrated water extract was kept at 10° C. for 48 hr to crystallize oxalic acid or oxalates. The supernatant was decanted off and again kept at 10° C. for 24 hr to crystallize remaining oxalic acid or oxalates. The supernatant from this solution was decanted, filtered and evaporated to dryness under vacuum to get oxalic acid or oxalate free Amaranth extract (2.2 Kg).

This oxalic acid or oxalate free Amaranth extract was further extracted with chloroform by cold extraction. The extract was filtered and evaporated to dryness under vacuum to get nitrate enriched Amaranth extract (1.6 Kg). See also extract preparation in FIG. 8.

Nitrate content of the extract was found to be 16% as determined by ion chromatography.

EXAMPLE 9

Enrichment of Nitrates in Amaranth Extract by Extraction with Ethylene Dichloride (EDC).

Fresh Amaranth were collected (100 Kg). Leaves and stem of fresh Amaranth were cleaned and crushed to make slurry. The slurry was treated with pectinase (1%) for 2 Hrs. The enzyme was deactivated by heating the slurry at 90° C. for 10 minutes. The extraction was performed with water using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract.

Concentrated water extract was kept at 10° C. for 48 hr to crystallize oxalic acid or oxalates. The supernatant was decanted off and again kept at 10° C. for 24 hr to crystallize remaining oxalic acid or oxalates. The supernatant from this solution was decanted, filtered and evaporated to dryness under vacuum to get oxalic acid or oxalate free Amaranth extract (2.2 Kg).

This oxalic acid or oxalate free Amaranth extract was further extracted with EDC for 8 hours in a soxhlet extractor. The extract was filtered and evaporated to dryness under vacuum to get nitrate enriched Amaranth extract (1.6 Kg). See also extract preparation in FIG. 9.

Nitrate content of the extract was found to be 17% as determined by ion chromatography.

EXAMPLE 10

Preparation of Amla Extract.

Fresh Amla fruits weighing 10 Kg were pulped and the pulp was extracted with methanol at 65° C. for 8 hours in a soxhlet apparatus. After the completion of extraction, the supernatant was filtered and concentrated at 60° C. to form concentrated methanol extract of Amla. Concentrated methanol extract was dried under vacuum at above 500 mm of mercury to get methanol extract of fresh Amla fruits (Yield: 500 gm). See also extract preparation in FIG. 10.

EXAMPLE 11

Amaranth eExtract Enriched with Amla Extract.

1.5 Kg of fresh Amaranth leaves extract (from Example 7) was taken in a beaker and dissolved in methanol (5 L). 150 gm of Amla extract (from Example 10) was added to this solution and stirred for 1 hr at 100 rpm using mechanical stirrer. The obtained mixture was evaporated to dryness under vacuum to get combined extract. See also extract preparation in FIG. 11

Nitrate content of this combined extract was 17%.

EXAMPLE 12

Method of Preparation of Amaranth Leaf Powder.

Figure 12:
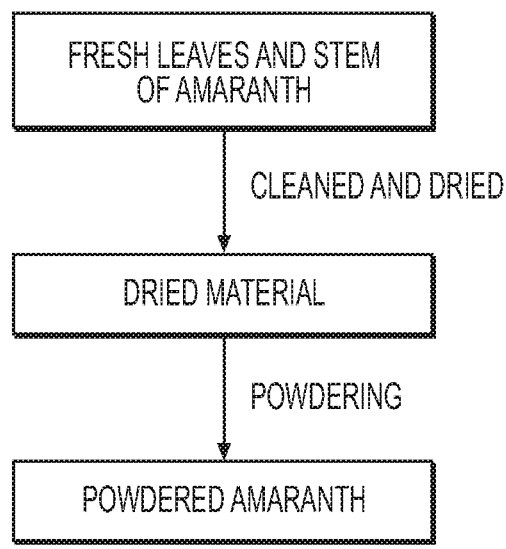
FIG. 12: Flow chart—Preparation of dried Amaranth leaf powder.

Fresh Amaranth were collected (100 Kg). Leaves of fresh Amaranth were cleaned and dried. Dried leaves were powdered to get Amaranth leaf powder. See also extract preparation in FIG. 12

EXAMPLE 13

Method of Preparation of Juice from Amaranth Leaves.

Fresh Amaranth leaves were collected (2 Kg). Leaves of fresh Amaranth were cleaned. The cleaned leaves were crushed in the screw expeller. The initial juice obtained on the tray of the screw expeller was collected in the feed tank under room temperature of 27° C. The initial juice was centrifuged to obtain filtrate which was collected and the residue which was removed. The collected filtrate was clarified in a rotating disc type clarifier (RPM—18000) to obtain final filtrate and some residue. After removing the residue, the final filtrate (clarified liquid juice of leaves of Amaranth) was collected with a yield 750 ml juice from 2 Kg Amaranth leaves. See also extract preparation in FIG. 13.

EXAMPLE 14

Preparation of Methanol Extract of Amaranth Fresh Leaves Using Different Varieties of Amaranth.

Fresh leaves and stem of *Amaranthus tricolor* were collected (100 Kg). Leaves and stem of fresh *Amaranthus tricolor* were cleaned and crushed. Crushed materials were filled in the Soxhlet extractor and extracted with methanol (300 L). The extraction was carried out for 5 hrs at a temperature of about 65° C. After the completion of extraction, the supernatant was filtered and concentrated in an Agitated thin film evaporator (ATFE) at a temperature of 60° C. to form concentrated methanol extract. Concentrated methanol extract was dried under vacuum at above 500 mm of mercury to get powder of methanol extract of fresh *Amaranthus tricolor* (Product 1) (Yield 2.1 Kg).

The nitrate content in methanol extract of fresh *Amaranthus* tricolour by HPLC was found to be 1.48%.

Methanol extract of different species of Amaranth were prepared followed by the same procedure as mentioned above.

Different species of *Amaranthus* that were used for the extraction are *Amaranthus caudatus, Amaranthus cruentus, Amaranthus blitum* and *Amaranthus viridis*. After methanol extraction of different species yields 1. Powder of methanol extract of fresh *Amaranthus caudatus* (Product II) (Yield 1.95 Kg).
   The nitrate content in methanol extract of fresh *Amaranthus caudatus* by HPLC was found to be 1.55%.
2. Powder of methanol extract of fresh *Amaranthus cruentus* (Product III) (Yield 2 Kg).
   The nitrate content in methanol extract of fresh *Amaranthus cruentus* by HPLC was found to be 1.53%.
3. Powder of methanol extract of fresh *Amaranthus blitum* (Product IV) (Yield 2.05 Kg).
   The nitrate content in methanol extract of fresh *Amaranthus blitum* by HPLC was found to be 1.5%.
4. Powder of methanol extract of fresh *Amaranthus viridis* (Product V) (Yield 2.15 Kg).
   The nitrate content in methanol extract of fresh *Amaranthus viridis* by HPLC was found to be 1.49%.

EXAMPLE 15

Enrichment of Nitrates in Amaranth (Different Varieties) Extract by Extraction with Hexane.

Fresh leaves and stem of *Amaranthus tricolor* were collected (100 Kg). Leaves and stem of fresh *Amaranthus tricolor* were cleaned and crushed to make slurry. The slurry was treated with pectinase (1%) for 2 Hrs. The enzyme was deactivated by heating the slurry at 90° C. for 10 minutes. The extraction was performed with water using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract.

Concentrated water extract was kept at 10° C. for 48 hr to crystallize oxalic acid or oxalates. The supernatant was decanted off and again kept at 10° C. for 24 hr to crystallize remaining oxalic acid or oxalates. The supernatant from this solution was decanted, filtered and evaporated to dryness under vacuum to get oxalic acid or oxalate free extract of *Amaranthus tricolor* (2.22 Kg).

This oxalic acid or oxalate free extract of *Amaranthus tricolor* was further extracted with hexane for 6 hours in a soxhlet extractor. The extract was filtered and evaporated to dryness under vacuum to get nitrate enriched extract of *Amaranthus tricolor* (Product I) (1.63 Kg).

Nitrate content of the extract was found to be 17.7% as determined by HPLC.

Nitrate enriched extract of different species of *Amaranthus* were prepared followed by the same procedure as mentioned above.

Different species of *Amaranthus* that were used for the extraction are *Amaranthus caudatus, Amaranthus cruentus, Amaranthus blitum* and *Amaranthus viridis*. After extraction of different species yields 1. Powder of nitrate enriched extract of fresh *Amaranthus caudatus* (Product II) (Yield 1.62 Kg)
The nitrate content in nitrate enriched extract of fresh *Amaranthus caudatus* by HPLC was found to be 17.9%.
2. Powder of nitrate enriched extract of fresh *Amaranthus cruentus* (Product III) (Yield 1.6 Kg)
The nitrate content in nitrate enriched extract of fresh *Amaranthus cruentus* by HPLC was found to be 18%.
3. Powder of nitrate enriched extract of fresh *Amaranthus blitum* (Product IV) (Yield 1.58 Kg)
The nitrate content in nitrate enriched extract of fresh *Amaranthus blitum* by HPLC was found to be 18.3%.
4. Powder of nitrate enriched extract of fresh *Amaranthus viridis* (Product V) (Yield 1.61 Kg)
The nitrate content in nitrate enriched extract of fresh *Amaranthus viridus* by HPLC was found to be 18.1%.

EXAMPLE 16

Determination of Nitrate and Nitrite Content in Amaranth by Ion Chromatography.

A 50 microliter aliquot of sample was pipette into a 300 microliter glass tube (Sci-Vi, Chromacol, Welwyn, UK). Acetonitrile (50 microliter) was added, and the tube with an autosampler limited-volume insert spring was put in a 4-ml WISP vial, capped, mixed and centrifuged at 2000 g for 2 min. The supernatant was injected for analysis.

882 Compact IC plus chromatograph (Metrohm, USA) fitted with a WISP autosampler (Waters, Watford, UK). The column was a Metrosep A Supp 5-150/4.0 ion-exchange column, 150 mm×4 mm (Metrohm), and the eluent was 1.7 mM Sodium bicarbonate ($NaHCO_3$), 1.8 mM Sodium carbonate ($Na_2CO_3$), pumped at 1.5 ml/min. Detection was by conductivity (DX100) and absorbance at 214 nm using a 441 detector fitted with a zinc lamp (Waters). Data was acquired and processed using an 840 data system (Waters).

EXAMPLE 17

Determination of Nitrate and Nitrite by HPLC Method.

Standard for nitrate ($NO_3$) was prepared by weighing 81.53 mg potassium nitrate (99% pure) in to 100 ml standard flask and made up to mark with water. 1 ml from the 100 ml solution was pipetted out into 50 ml standard flask and made up to mark with water.

Standard for nitrite ($NO_2$) was prepared by weighing 92.49 mg potassium nitrite (96% pure) in to 100 ml standard flask and made up to mark with water. 1 ml from the 100 ml solution was pipetted out into 50 ml standard flask and made up to mark with water. Again 1 ml from the 50 ml solution was pipetted out into 50 ml standard flask and again made up to mark with water.

Added 1 ml standard of nitrite and 1 ml mobile phase A (Weighed 1.3 g of the Tetra Butyl ammonium Hydroxide Solution (10% aqu) in to 1000 ml standard flask. Made up to mark with Water. Then PH adjusted to 2.50 with Con: $H_2SO_4$), 200µ Griess A (Weighed 50.00 mg sulphanilic acid and 1.5 ml acetic acid and 3 ml purified water was added and dissolved) and after 2 min added 200µ Griess B (Weighed 4.00 mg 1-naphthylamine and 4.0 ml acetic acid was added and dissolved) in to a plastic tube. Filtered through 0.45 µm membrane filter before injection.

Sample (Amaranth extract) was prepared by weighing accurately 20-25 mg of the extract powder to 25 ml std flask and made up the with demineralized water. Filtered through 0.45 Micron membrane filter and divided into 2 portions. One portion was used for Nitrate and other portion was used for Nitrite determinations.

$NO_3$ was analyzed by HPLC on a BETASIL C-18 column (250×4.6 mm) using Tetra butyl ammonium hydroxide in De-ionized water, acetonitrile and methanol as mobile phase and Photo diode array detection at 222 nm. $NO_2$ was analysed at 520 nm using the same conditions.

$$\text{Nitrite \%} = \frac{\text{Area of Nitrite peak in sample} \times \text{Amount of } Std \times \text{Purity of } Std}{\text{Area of Nitrite peak in Standard} \times \text{Weight of the Sample}}$$

$$\text{Nitrate \%} = \frac{\text{Area of Nitrate peak in sample} \times \text{Amount of } Std \times \text{Purity of } Std}{\text{Area of Nitrate peak in Standard} \times \text{Weight of the Sample}}$$

EXAMPLE 18

Determination of Nitric Oxide (NO).

Total NO content in plasma can be interpreted as the sum of total nitrate ($NO_3$) and nitrite ($NO_2$) in plasma.

(Journal of Medical sciences (2010):3 (3): 153-159, Plasma Endothelin—1, Homocysteine, and Oxide Levels in a Multiethnic Hypertensive Cochot from the United Arab Emirates.)

NO levels was recorded as the sum of the two major metabolites of NO, nitrite and nitrate.

EXAMPLE 19

Determination of Total Oxalic Acid Content.

Oxalic acid was estimated by high performance liquid chromatography (HPLC-DAD) on a C18 column (250×4.6 mm, Gemini 5 µm, USA.). The mobile phase was 5 mM H2SO4 and used under isocrating condition with an eluent flow rate of 1 ml/min. Oxalic acid was detected at 210 nm.

Standard was prepared by weighing 5 mg of standard oxalic acid (95% purity) and was made up to 50 ml with 6 mM H2SO4. Sample was prepared by weighing 50 mg of the dry extract of Amaranth and was made up to 50 ml with 6 mM H2SO4. Both the sample and standard were filtered separately through a 0.2 µm membrane filter before injection into the HPLC column. The injection volume was 20 µl. Oxalic acid was detected at 210 nm. By comparing the area of standard and sample, the percentage of oxalic acid present in the sample was quantified.

$$\text{Oxalic acid \%} = \frac{\text{Area of sample} \times \text{amount of standard} \times \text{purity of standard}}{\text{Amount of sample} \times \text{Area of standard}}$$

EXAMPLE 20

Determination of Potassium Content.

Potassium was determined by Atomic absorption spectroscopy (AAS). A 100 ppm solution of potassium Standard (KCl) was prepared. Seven different standards of potassium in different concentrations were prepared by simple dilution of the above 100 ppm solution. The sample solution and standard were measured in the AAS machine at 766.5 nm to create a calibration curve for determination of potassium content in the sample solutions.

EXAMPLE 21

Preparation of Fast Dissolving Tablets.

Fast dissolving tablets were made by mixing Fast-Melt (119.2 gm) with amaranth nitrate enriched (18% nitrate) extract (80 gm) (as per Example 7). Magnesium stearate (0.8 gm) was added to the mixture before tablet punching. Tablets weighing 200 mg were punched on automatic tablet punch machine using 8 mm die to get 5 Kg hardness. The final composition of each tablet was 119.2 mg F-Melt, 80 mg extract (approx. 14.4 mg nitrate) and 0.8 mg of magnesium stearate. Disintegration time of tablets was approximately 30 seconds.

EXAMPLE 22

Preparation of Fast Dissolving Tablets.

Fast dissolving tablets were made by mixing Fast-Melt (745 gm) with amaranth nitrate enriched (18% nitrate) extract (500 gm) prepared as per example 7. Magnesium stearate (5 gm) was added to the mixture before tablet punching. Tablets weighing 1250 mg were punched on automatic tablet punch machine using 12 mm die to get 5 Kg hardness. The final composition of each tablet was 745 mg F-Melt, 500 mg extract (approx. 90 mg nitrate) and 5 mg of magnesium stearate. Disintegration time of tablets was approximately 30 seconds.

Similarly fast melt tablets were made by substitute the above extract with
1. Methanol extract of fresh leaves of Amaranth (1.5% nitrate) (Final composition of Fast melt tablet contain 750 mg F-Melt, 500 mg extract (approx 7.5 mg nitrate) and 5 mg of magnesium stearate)
2. Water extract of fresh leaves of Amaranth (1.6% nitrate) (Final composition of Fast melt tablet contain 750 mg F-Melt, 500 mg extract (approx 8 mg nitrate) and 5 mg of magnesium stearate)
3. Methanol extract of dried leaves of Amaranth (1.65% nitrate) (Final composition of Fast melt tablet contain 750 mg F-Melt, 500 mg extract (approx 8.25 mg nitrate) and 5 mg of magnesium stearate)
4. Water extract of dried leaves of Amaranth (1.7% nitrate) (Final composition of Fast melt tablet contain 750 mg F-Melt, 500 mg extract (approx 8.5 mg nitrate) and 5 mg of magnesium stearate)
5. Pectinase treated water extract of fresh leaves of Amaranth (2% nitrate) (Final composition of Fast melt tablet contain 750 mg F-Melt, 500 mg extract (approx 10 mg nitrate) and 5 mg of magnesium stearate)
6. Extract of *Amaranthus blitum* with enriched nitrate (18.3% nitrate) (Final composition of Fast melt tablet contain 750 mg F-Melt, 500 mg extract (approx 91.5 mg nitrate) and 5 mg of magnesium stearate)
7. Extract of *Amaranthus viridus* with enriched nitrate (18.1% nitrate) (Final composition of Fast melt tablet contain 750 mg F-Melt, 500 mg extract (approx 90.5 mg nitrate) and 5 mg of magnesium stearate)

EXAMPLE 23

Preparation of Chewing Gum.

Chewing gums were prepared by adding amaranth nitrate enriched extract (80 mg for one chewing gum) to the base material (920 mg for one chewing gum). The base material consists of polyvinyl acetate in an amount by weight of about 38%, natural rubber in an amount by weight of about 10%, partially hydrogenated soybean oil in an amount by weight of about 11%, polyisobutylene in an amount by weight of about 12%, dicalcium phosphate in an amount by weight of about 13.92%, triacetin in an amount by weight of about 3%, mono-di-glycerides in an amount by weight of about 7%, liquid glucose in an amount by weight of about 5%, and BHT (butylated hydroxyl toluene) in an amount by weight of about 0.08%.

The chewing gum components (except liquid glucose and BHT) were mixed in a mixer with strong horizontally placed Z-blades, which processes the components into a homogeneous gum mass. The mixer was heated to a temperature of approx. 50-60° C. The mixing process starts with mixing and melting the gum base for 3 minutes.

The liquid glucose was then added and mixed for 4 minutes. Subsequent, the amaranth nitrate enriched extract were added and the mixture was mixed for further 6 minutes. The BHT was then added and mixed for further 5 minutes.

When the mixing was completed, the gum mass was taken out onto trays and rolled out to a 1-2 cm thick sheet. The chewing gum mass was subsequent cooled for approx. 15-20 minutes until the right texture of the gum mass was achieved.

The formed and cooled chewing gum cores were then coated and polished with a coating suspension in a round stainless steel coating kettle that rotate during the coating and polishing process. The coating suspension consists of Xylitol (58.2%), Mannitol (10.6%), Gelatin (1.2%), Titanium dioxide (0.9%), Acesulfame K (0.1%) and water (29%).

The polishing was done in rotating kettles in which carnauba wax (0.1%) was added to the coated chewing gums in one portion. Polishing was done until a shinning surface is achieved, typically for 10-20 minutes. Each chewing gum contained 80 mg of extract (approx. 14.4 mg nitrate).

EXAMPLE 24

Nitric Oxide Level in Rats.

18 albino rats (Sprague-Dawley (SD) strain) weighing 200-250 gm were taken for the study. The animals were acclimatized to the animal house condition (24±2° C. temperature, 65% relative humidity, 12 hr light/dark cycle) for one week. The animals were divided into three groups comprising of six animals in each group. The animals were fasted overnight and blood was collected to determine the baseline nitric oxide level. The animals were treated as follows:
Group 1: Vehicle control
Group 2: Amaranth dried leaves powder—1 gm/kg
Group 3: Amaranth nitrate enriched extract (from example 7)—100 mg/kg After 30 minutes of feeding, blood was collected from all the animals in EDTA (ethylenediaminetetraaceticacid) coated tubes and plasma was separated immediately by centrifuging the tubes at 4000 rpm (rotations per minute) for 10 minutes. The plasma was stored below −80° C. until analysis.

The nitric oxide (NO) content of the plasma was reported as µmol/L.

| S. No. | Groups | Baseline Nitric oxide level (µmol/L) | Nitric oxide level after 30 min (µmol/L) |
|---|---|---|---|
| 1. | Vehicle control | 18.2 | 18.4 |
| 2. | Amaranth dried leaves powder | 17.9 | 18.2 |
| 3. | Amaranth nitrate enriched extract (from example 7) | 18.6 | 42.3 |

EXAMPLE 25

Nitric Oxide Level in Mice.

18 swiss albino mice weighing 25-30 gm were taken for the study. The animals were acclimatized to the animal house condition (24±2° C. temperature, 65% relative humidity, 12 hr light/dark cycle) for one week. The animals were divided into three groups comprising of six animals in each group. The animals were fasted overnight and blood was collected to determine the baseline nitric oxide level. The animals were treated as follows:
Group 1: Vehicle control
Group 2: Amaranth dried leaves powder (from example 12)—1 gm/kg
Group 3: Amaranth extract enriched with Amla extract (from example 11)—200 mg/kg After 30 minutes of feeding, blood was collected from all the animals in EDTA (ethylenediaminetetraaceticacid) coated tubes and plasma was separated immediately by centrifuging the tubes at 4000 rpm for 10 minutes. The plasma was stored below −80° C. until analysis.

The nitric oxide (NO) content of the plasma is reported as µmol/L.

| S. No. | Groups | Baseline Nitric oxide level (µmol/L) | Nitric oxide level after 30 min (µmol/L) |
|---|---|---|---|
| 1. | Vehicle control | 21.9 | 21.7 |
| 2. | Amaranth dried leaves powder (from example 12) | 20.8 | 22.6 |
| 3. | Amaranth extract enriched with Amla extract (from example 11) | 21.6 | 76.4 |

EXAMPLE 26

Oral Toxicity Study in Rats.

This study was conducted as per OECD Guidelines (Organisation for economic co-operation and development) for Testing of chemicals (No.-408). 100 Wistar albino rats (50 males/50 females) were divided into four groups of 20 animals (10 males and 10 Females) in each and two groups (Satellite groups) of 10 animals (5 males and 5 Females) in each group. The animals were acclimatized for seven days before the commencement of dosing. Three groups of 20 rats each (10 male and 10 female) were administered with amaranth nitrate enriched extract (from example 8) at the dosage levels of 100 mg/kg body weight (low dose), 500 mg/kg b.wt (body weight) (intermediate dose) and 1000 mg/kg body weight (high dose) respectively for seven days a week for 90 days with the help of cannula attached with the syringe. Similarly, fourth group of 20 rats (10 male and 10 female rats) were orally administered with corn oil only (vehicle) for 90 days and was designated as control group.

Two additional satellite groups of 10 rats (5 male and 5 female) each were also kept and designated as 'Satellite control' and 'Satellite high dose' and were administered with corn oil (vehicle) and amaranth nitrate enriched extract (1000 mg/kg) respectively for 90 days. After terminal sacrifice of the test and control group animals, both Satellite group animals (Satellite control and Satellite high dose) were kept under observation for an additional 28 days, to check the reversibility, persistence or delayed toxic effect, if any. The animals were observed daily for behavior, appearance and toxicological signs and symptoms. Blood was collected from all the animals before terminal sacrifice for detailed hematological and biochemical evaluation. Urine samples were also collected from all animals at the termination of the experiment. Criteria used to evaluate compound related effects included; appearance, behavior, morbidity, mortality, body weights, Feed consumption, hematological and biochemical analysis, urine analysis, organ weights, necropsy and histopathology.

No treatment related toxic sign and symptoms were observed in low dose (100 mg/kg body weight), intermediate dose (500 mg/kg body weight), high dose (1000 mg/kg body weight.) and satellite high dose (1000 mg/kg body weight) group animals when compared to their respective control counter parts. Body weights of all the test and control group animals were recorded weekly. Body weight gain of all the treatment groups and satellite group animals (LD, ID, HD & satellite HD) was comparable to their control counterparts. Feed consumption of the animals of low dose, intermediate dose, high dose and satellite high dose were comparable to the control group and satellite control group animals.

There were no variations in the haematological parameters of animals of low dose (100 mg/kg Body weight), intermediate dose (500 mg/kg body weight), high dose (1000 mg/kg body weight) and satellite high dose (1000 mg/kg body weight) groups when compared to the control group animals. Similarly, the biochemical parameters of animals of all the treatment groups i.e. low dose, intermediate dose and high dose were comparable to the biochemical parameters of the control group animals at the terminal sacrifice. The biochemical parameters of satellite high dose group were also comparable to its satellite control counterparts. The heamatological as well as biochemical parameters of test groups were not significantly different from respective control groups.

Urine samples were collected from all animals at the termination of the experiment. No significant changes were noted in the urine parameters of any of the dose group animals when compared to the control group. Animals of satellite groups were sacrificed after 28 days post treatment. None of the animals died during the study in any of the treated groups as well as the satellite groups. After completion of dosing period of 90 days, all the groups (treatment and control) except both the satellite groups were sacrificed and were examined for gross pathological findings. Organs of all the animals (treatment and control) were trimmed of any adherent fat tissue and their weights taken. Organ weights of animals of all treatment groups were comparable to their respective control counter parts. There were no significant histopathological changes in the animals of low dose group, intermediate dose group, high dose group and satellite high dose group when compared to their control counterparts.

In this study, the repeated administration of amaranth nitrate enriched extract for 90 days, by oral route, to wistar rats at the dosage level of 1000 mg/kg body weight did not induce any observable toxic effects, when compared to its corresponding control group of animals.

EXAMPLE 27

Nitric Oxide Level in Human Subjects.

18 healthy human volunteers (age 35-55 years) were taken for the study. The subjects were put on standard diet (devoid of nitrate/nitrite containing food) one week prior to the study. The subjects were divided into three groups comprising of six subjects in each group. The subjects were fasted overnight and blood was collected to determine the baseline nitric oxide level. After blood collection, the subjects were treated as follows:

Group 1: Vehicle control

Group 2: Amaranth fresh leaves as such—100 gm

Group 3: Amaranth fast dissolving tablet containing amaranth nitrate enriched extract (14.4 mg nitrate per tablet pepared as per example 21 and extract used for making the tablet prepared as per example 7)

After 30 minutes of feeding, blood was collected from all the subjects in EDTA (ethylene di amine tetra acetic acid) coated tubes and plasma was separated immediately by centrifuging the tubes at 4000 rpm for 10 minutes. The plasma was stored below $-80°$ C. until analysis for nitric oxide content. The nitric oxide (NO) content of the plasma is reported as µmol/L.

| S. No. | Groups | Baseline Nitric oxide level (µmol/L) | Nitric oxide level after 30 min (µmol/L) |
|---|---|---|---|
| 1. | Vehicle control | 28.5 | 28.2 |
| 2. | Amaranth fresh leaves as such | 29.2 | 30.1 |
| 3. | Amaranth fast dissolving tablet(Fast melt prepared as per Example 21 and extract used for making the tablet prepared as per example 7) | 29.1 | 78.9 |

EXAMPLE 28

Anti-hypertensive Activity in Human Subjects.

10 Subjects (6 males and 4 females) aged 40 to 60 years with pre-hypertension [SBP (systolic blood pressure), 130 to 140 mmHg and DBP (diastolic blood pressure), 85 to 90 mmHg) or hypertension (SBP (systolic blood pressure), 140 mmHg or higher and DBP (diastolic blood pressure), 90 mmHg or higher) were enrolled in the study. Exclusion criteria included pregnant and lactating women, people who had received trace element supplements in the previous three months, people receiving gastric or diuretic treatments, patients with acute renal failure, or people with recent history of surgery or acute infections. All subjects were informed of the purposes of the study, were free to ask questions throughout the study, and signed an informed consent form witnessed by one of the investigators.

| S. No. | Subjects | Baseline blood pressure (SBP/DBP in mmHg) | Blood pressure after 15 days (SBP/DBP in mmHg) | Blood pressure after 30 days (SBP/DBP in mmHg) |
|---|---|---|---|---|
| 1. | Subject 1 | 138/87 | 135/84 | 130/82 |
| 2. | Subject 2 | 142/90 | 138/88 | 133/84 |
| 3. | Subject 3 | 140/89 | 137/87 | 131/83 |
| 4. | Subject 4 | 139/88 | 136/86 | 132/83 |
| 5. | Subject 5 | 143/91 | 138/88 | 134/85 |
| 6. | Subject 6 | 141/90 | 136/87 | 132/84 |
| 7. | Subject 7 | 139/90 | 135/83 | 129/81 |
| 8. | Subject 8 | 138/86 | 134/83 | 128/80 |
| 9. | Subject 9 | 142/90 | 137/87 | 131/84 |
| 10. | Subject 10 | 142/90 | 136/86 | 132/83 |

The patients were provided with a bottle containing 60 fast melt mouth dissolving tablets (from Example 21) and instructed to take one tablet twice daily at 12 hour interval for 30 days. Eating habits were not restricted during the treatment. However, to avoid possible interference with the effects of PG, the consumption of vitamin supplements and functional foods was prohibited during the trial. Each subject's BP (blood pressure) was measured at the beginning, 15 days and end of the trial. Their BP (blood pressure) was measured using a digital BP analyzer and recorded as the average of two measurements. Measurements were always made at the same place and time after 15 min of rest.

EXAMPLE 29

Swimming Endurance Test in Mice.

For swimming endurance study, prior to experiment, each mouse was tested for feasibility testing. All mice in swimming groups could swim. The mice were divided into 3 groups comprising of 6 animals in each group. Following treatment was given to the respective group of mice:

Group 1: Vehicle control

Group 2: Amaranth dried leaves powder (from example 12)—1 gm/kg

Group 3: Amaranth nitrate enriched extract (from example 8)—100 mg/kg

Treatment was given for four weeks.

All mice were subjected to swim in a water pool (48×28×24 inch), filled 19 inch deep of water maintained at 25° C. During swimming testing, each mouse was fixed four paper clips with a plastic string on the tail. The paper clips and plastic string weighted about 1.81 grams. Bearing this weight, all mice were forced to swim very hard. All mice were subjected to swim until exhaustion (cease movement of limbs and float). The maximum time swimming until mice exhausted was used as the index of swimming endurance capacity. The test was conducted in the beginning and then weekly till four weeks. Blood was also collected in the beginning and after each week to determine the nitric oxide level in plasma.

| | | Swimming endurance (seconds) | | | | |
|---|---|---|---|---|---|---|
| S. No. | Groups | Base-line | 1 Week | 2 Weeks | 3 Weeks | 4 Weeks |
| 1. | Vehicle control | 130 | 126 | 128 | 130 | 127 |
| 2. | Amaranth dried leaves powder (from example 12) | 132 | 146 | 168 | 172 | 179 |
| 3. | Amaranth nitrate enriched extract (from example 8) | 128 | 155 | 171 | 185 | 193 |

Nitric Oxide Level

| | | Nitric oxide level (μmol/L) | | | | |
|---|---|---|---|---|---|---|
| S. No. | Groups | Base-line | 1 Week | 2 Weeks | 3 Weeks | 4 Weeks |
| 1. | Vehicle control | 17.6 | 17.3 | 18.2 | 18.0 | 17.9 |
| 2. | Amaranth dried leaves powder (from example 12) | 17.9 | 18.1 | 18.3 | 17.7 | 17.9 |
| 3. | Amaranth nitrate enriched extract (from example 8) | 17.7 | 32.1 | 46.5 | 51.3 | 56.9 |

EXAMPLE 30

Running Endurance Test in Mice.

For running endurance study, individual mouse was trained for running on a Rota-Rod apparatus (treadmill) for three days prior to running study. During training, the speed of the Rota-rod was increased incrementally to make animals exercise more intensely and running for at least one minute. The mice were divided into 3 groups comprising of 6 animals in each group. Following treatment was given to the respective group of mice:

Group 1: Vehicle control
Group 2: Amaranth dried leaves powder (from example 12)—1 gm/kg
Group 3: Amaranth nitrate enriched extract (from example 9)—100 mg/kg Treatment was given for four weeks.

The Rota-Rod treadmills had five testing zones, each zone had a photo bean that sensed when the animal dropped off the treadmills which was connected with computer to calculate running time on the treadmills automatically. The speed of the Rota-rod was set to 35 RPM (rotation per minute). The maximum time running until exhaustion (drops from the Rota-rod) was used as the index of running endurance capacity. The maximum time of running until exhaustion in each mouse was recorded. The test was conducted in the beginning and then weekly till four weeks.

| | | Running endurance (seconds) | | | | |
|---|---|---|---|---|---|---|
| S. No. | Groups | Base-line | 1 Week | 2 Weeks | 3 Weeks | 4 Weeks |
| 1. | Vehicle control | 452 | 445 | 454 | 450 | 448 |
| 2. | Amaranth dried leaves powder (from example 12) | 436 | 451 | 472 | 481 | 486 |
| 3. | Amaranth nitrate enriched extract (from example 9) | 441 | 468 | 489 | 497 | 510 |

EXAMPLE 31

Sexual Performance Study in Rats.

Twelve male wistar rats (200-250 gm) were randomized into 2 groups comprising of 6 animals each. The animals were treated for 30 days with vehicle/extract and various test parameters were evaluated.

Group I (vehicle only) served as control.
Group II Amaranth extract enriched with amla extract (from example 11)—100 mg/Kg (p.o.) daily Orientation Behavior Analysis The analysis of orientation activity was carried out and analyzed in three segments. Orientation behavior of male rats was determined using following method of scoring:
Orientation towards female—(1 for every sniffing and 2 for every licking)
Orientation towards self—(1 for non-genital grooming and 2 for genital grooming)
Orientation towards environment—(1 for exploration, 2 for rearing and 3 for climbing)

Rats were observed daily for their orientation activity. The cumulative score after 0, 15, 30 days of the treatment were recorded.

Sexual Behavior Analysis

Male rat was placed in the observation glass chambers in order to acclimatize it with the cage environment. Sexually receptive female rat was then allowed to enter the test cage silently from a side door inside the cage. The behavioral observations were carried out taking into account the following parameters.

Mounting Behavior—It was determined and characterized by following parameters.

(A) Mount frequency—average number of mount during 30 min observation.

(B) Mount latency—The leg time from the introduction of female in the cage to first mount.

Intromission Behavior—It was evaluated as follows.

(A) Intromission frequency—average number of Intromission during 30 min observation.

(B) Intromission latency—Intromission latency (IL) was considered as the time for first intromission after introduction of female in the cage.

Penile Erection Index

Penile Erection (PE) was determined when the rats bent down to lick their erect penis during the observation period. Penile erection index (PI) was determined by multiplying the percentage of rats exhibiting at least one episode of penile erection during 30-min observation period with the mean number of penile erections.

PI=% of rats exhibiting penile erection×Mean number of erections.

TABLE

Effect of enriched amaranth extract on orientation activities in male rats

| Parameters for sexual behavior analysis | Groups | 0 days | 15 days of treatment | 30 days of treatment |
|---|---|---|---|---|
| Mean activity Score Towards Female (Licking & Anogenital smelling) | Vehicle control | 7.5 | 7.6 | 7.5 |
| | Amaranth extract enriched with Amla extract | 7.4 | 11.2 | 16.3 |
| Mean activity Score Towards Environment | Vehicle control | 13.2 | 13.3 | 13.6 |
| | Amaranth extract enriched | 13.3 | 16.5 | 22.2 |

TABLE-continued

Effect of enriched amaranth extract on orientation activities in male rats

| Parameters for sexual behavior analysis | Groups | 0 days | 15 days of treatment | 30 days of treatment |
|---|---|---|---|---|
| (Exploration, Rearing and Climbing) Mean activity Score Towards Self (Nongenital grooming and Genital grooming) | with Amla extract Vehicle control Amaranth extract enriched with Amla extract | 8.1 7.9 | 8.0 12.6 | 8.1 15.3 |

TABLE

Effect of enriched amaranth extract on sexual performance parameters in male rats

| Parameters for sexual behavior analysis | Groups | 0 days | 15 days of treatment | 30 days of treatment |
|---|---|---|---|---|
| Mount latency (time in seconds) | Vehicle control | 194.3 | 195.6 | 195.2 |
| | Amaranth extract enriched with Amla extract | 193.5 | 160.2 | 124.3 |
| Mount frequency | Vehicle control | 3.3 | 3.5 | 3.8 |
| | Amaranth extract enriched with Amla extract | 3.4 | 10.5 | 12.4 |
| Intromission latency (time in seconds) | Vehicle control | 305.2 | 304.3 | 302.6 |
| | Amaranth extract enriched with Amla extract | 309.5 | 275.3 | 254.4 |
| Intromission frequency | Vehicle control | 1.6 | 1.7 | 1.7 |
| | Amaranth extract enriched with Amla extract | 1.5 | 4.2 | 6.3 |
| Penile Erection Index (PI) | Vehicle control | 23.3 | 22.7 | 24.5 |
| | Amaranth extract enriched with Amla extract | 21.5 | 45.3 | 62.6 |

EXAMPLE 32

Nitrate ($NO_3$) Nitrite ($NO_2$) and Nitric Oxide (NO) Content in Plasma of Human Subjects 32 Healthy human volunteers (age 35-55 years) were taken for the study. The subjects were put on standard diet one week prior to the study. The subjects were divided into 8 groups comprising of four subjects in each group. The subjects were fasted overnight and the blood was collected to determine the baseline $NO_3$ and $NO_2$ levels. After baseline blood collection, the subjects were treated as follows:

Group 1: Vehicle Control

Group 2: Amaranth leaves fresh juice as such—100 ml (100 mg Nitrate/100 ml of juice) (Prepared as per example No-13)

Group 3: Amaranth fast dissolving tablet containing Methanol extract of Amaranth fresh leaves (7.5 mg nitrate per tablet) (Tablet prepared as per example No. 22 and extract used for preparing the tablet is as per example 1)

Group 4: Amaranth fast dissolving tablet containing Methanol extract of Amaranth dried leaves (8.25 mg nitrate per tablet) (Tablet prepared as per example No. 22 and extract used for preparing the tablet is as per example 3)

Group 5: Amaranth fast dissolving tablet containing water extract of Amaranth fresh leaves (8 mg nitrate per tablet) (Tablet prepared as per example No 22 and extract used for preparing the tablet is as per example 2)

Group 6: Amaranth fast dissolving tablet containing water extract of Amaranth dried leaves (8.5 mg nitrate per tablet) (Tablet prepared as per example No 22 and extract used for preparing the tablet is as per example 4)

Group 7: Amaranth fast dissolving tablet containing Pectinase treated water extract of Amaranth fresh leaves (10 mg nitrate per tablet) (Tablet prepared as per example No 22 and extract used for preparing the tablet is as per example 5)

Group 8: Amaranth fast dissolving tablet containing amaranth nitrate enriched extract (90 mg nitrate per tablet) (Tablet prepared as per example No 22 and extract used for preparing the tablet is as per example 7)

All subjects were allowed to consume the water/Juice orally (Group No-1 to 2). Amaranth Tablet were kept in oral cavity and allow to dissolve (Group No-3 to 8).

After 1 hour, 2 hour and 3 hour from feeding of tablet/juice/vehicle, blood was drawn from all the subjects in EDTA coated tubes. Plasma was separated immediately by centrifuging the tubes at 5000 rpm for 15 min. The plasma samples were stored below −80 degree Celsius until analysis. The plasma thus obtained was deproteinized using Acetonitrile and the supernatant liquid was used for nitrate/nitrite determination using HPLC. $NO_3$ was analyzed by HPLC on a BETASIL C-18 column (250×4.6 mm) using Tetra butyl ammonium hydroxide in De-ionized water, acetonitrile and methanol as mobile phase and Photo diode array detection at 222 nm. $NO_2$ was analysed at 520 nm using the same conditions. The $NO_3$ and $NO_2$ levels in plasma were reported as μmol/L.

TABLE

Nitrate ($NO_3$) content in plasma

| SI NO | Groups | Baseline $NO_3$ levels (μmol/l) | $NO_3$ levels after 1 hour (μmol/l) | $NO_3$ levels after 2 hour (μmol/l) | $NO_3$ levels after 3 hour (μmol/l) |
|---|---|---|---|---|---|
| 1. | Vehicle Control | 28.92 | 28.95 | 27.88 | 28.81 |
| 2. | Amaranth fresh juice as such | 28.55 | 30.11 | 29.45 | 28.56 |
| 3. | Amaranth fast dissolving tablet containing methanol extract of fresh leaves | 27.88 | 30.12 | 29.88 | 28.65 |
| 4. | Amaranth fast dissolving tablet containing water extract of fresh leaves | 26.55 | 30.19 | 30.02 | 28.89 |

TABLE-continued

Nitrate (NO₃) content in plasma

| SI NO | Groups | Baseline NO₃ levels (μmol/l) | NO₃ levels after 1 hour (μmol/l) | NO₃ levels after 2 hour (μmol/l) | NO₃ levels after 3 hour (μmol/l) |
|---|---|---|---|---|---|
| 5. | Amaranth fast dissolving tablet containing methanol extract of dried leaves. | 29.52 | 33.20 | 30.25 | 29.56 |
| 6. | Amaranth fast dissolving tablet containing water extract of dried leaves | 29.10 | 32.8 | 31.02 | 29.77 |
| 7. | Amaranth fast dissolving tablet containing pectinase treated water extract of fresh leaves | 29.11 | 32.92 | 31.95 | 30.10 |
| 8. | Amaranth fast dissolving tablet containing enriched extract of nitrate | 28.88 | 174.40 | 110.22 | 70.89 |

TABLE

Nitrite (NO₂) content in plasma

| SI No | Groups | Base line NO₂ levels (μmol/l) | NO₂ levels after 1 hour (μmol/l) | NO₂ levels after 2 hour (μmol/l) | NO₂ levels after 3 hour (μmol/l) |
|---|---|---|---|---|---|
| 1. | Vehicle Control | 0.19 | 0.20 | 0.23 | 0.18 |
| 2. | Amaranth fresh juice as such | 0.21 | 0.25 | 0.24 | 0.20 |
| 3. | Amaranth fast dissolving tablet containing methanol extract of fresh leaves | 0.20 | 0.27 | 0.26 | 0.24 |
| 4. | Amaranth fast dissolving tablet containing water extract of fresh leaves | 0.21 | 0.29 | 0.27 | 0.25 |
| 5. | Amaranth fast dissolving tablet containing methanol extract of dried leaves. | 0.19 | 0.28 | 0.27 | 0.24 |
| 6. | Amaranth fast dissolving tablet containing water extract of dried leaves | 0.21 | 0.31 | 0.35 | 0.30 |
| 7. | Amaranth fast dissolving tablet containing pectinase treated water extract of fresh leaves | 0.19 | 0.30 | 0.28 | 0.25 |
| 8. | Amaranth fast dissolving tablet containing enriched extract of nitrate | 0.20 | 1.20 | 0.98 | 0.60 |

TABLE

Total nitric oxide (NO) content in plasma

| SI NO | Groups | Base line NO levels (μmol/l) | NO levels after 1 hour (μmol/l) | NO levels after 2 hour (μmol/l) | NO levels after 3 hour (μmol/l) |
|---|---|---|---|---|---|
| 1. | Vehicle Control | 29.11 | 29.15 | 28.11 | 28.99 |
| 2. | Amaranth fresh juice as such | 28.76 | 30.36 | 29.69 | 28.76 |
| 3. | Amaranth fast dissolving tablet containing methanol extract of fresh leaves | 28.08 | 30.39 | 30.14 | 28.89 |
| 4. | Amaranth fast dissolving tablet containing water extract of fresh leaves | 26.76 | 30.48 | 30.29 | 29.14 |

TABLE-continued

Total nitric oxide (NO) content in plasma

| SI NO | Groups | Base line NO levels (µmol/l) | NO levels after 1 hour (µmol/l) | NO levels after 2 hour (µmol/l) | NO levels after 3 hour (µmol/l) |
|---|---|---|---|---|---|
| 5. | Amaranth fast dissolving tablet containing methanol extract of dried leaves. | 29.71 | 33.48 | 30.52 | 29.80 |
| 6. | Amaranth fast dissolving tablet containing water extract of dried leaves | 29.31 | 33.11 | 31.37 | 30.07 |
| 7. | Amaranth fast dissolving tablet containing pectinase treated water extract of fresh leaves | 29.30 | 33.22 | 32.23 | 30.35 |
| 8. | Amaranth fast dissolving tablet containing enriched extract of nitrate | 29.08 | 175.60 | 111.2 | 71.49 |

Amaranth fresh juice consumption as such slightly increased the $NO_3$ content after one hour. Methanol extract from amaranth fresh leaves and dried leaves also showed a slight increase in $NO_3$ content. Tablet made with pectinase treated water extract of fresh leaves of Amaranth shown a little more increase than the other tablets consumptions. But after consumption of fast dissolving tablet containing Amaranth extract enriched with nitrate, $NO_3$ level increased to 6 times the baseline value after 1 hour and the increase from base line is maintained up to 3 hour. There was no significant change in $NO_3$ level after administering the vehicle.

In case of $NO_2$ also, the fast dissolving tablet containing Amaranth extract enriched with nitrate, increased the $NO_2$ level more than 6 times and the higher levels maintained for 3 hours. Amaranth fresh juice consumption as such slightly increased the $NO_2$ content after one hour. Methanol extract from amaranth fresh leaves and dried leaves also showed a slight increase in $NO_2$ content. Here also vehicle did not influence $NO_2$ level in the subjects.

Overall conclusion is that the increased levels of $NO_3$ and $NO_2$ increase observed in Amaranth fast dissolving tablet was more when compared with levels of nitrate and nitrite in Amaranth fresh juice, and methanol extract from fresh of dried leaves. The increase in total nitric oxide (NO) content of "Amaranth fast dissolving tablet containing enriched extract of nitrate" was 6 times from base line and it remained increased for 3 hours. Total NO is determined from the sum of total $NO_3$ and $NO_2$. (ie. Level of $NO_3$ and $NO_2$ can be interpreted as a measure of NO level in human body) So an increase in $NO_3$ and $NO_2$ level is interpreted as an increase in NO level. NO levels was recorded as the sum of the two major metabolites of NO, nitrite and nitrate.

EXAMPLE 33

Nitrate ($NO_3$), Nitrite ($NO_2$) and Nitric Oxide (NO) Content in Saliva of Human Subjects 32 Healthy human volunteers (age 35-55 years) were taken for the study. The subjects were put on controlled diet, one week prior to the study. The subjects were divided into eight groups comprising of four subjects in each group. The subjects were fasted overnight and saliva was collected to determine the base line $NO_3$ and $NO_2$ levels. After saliva collection, the subjects were treated as follows:

Group 1: Vehicle Control.

Group 2: Amaranth leaves fresh juice as such—100 ml (100 mg Nitrate/100 ml of juice) (Prepared as per example No. 13).

Group 3: Amaranth fast dissolving tablet containing Methanol extract of Amaranth fresh leaves (7.5 mg nitrate per tablet) (Tablet prepared as per example No 22 and extract used for preparing the tablet is as per example 1).

Group 4: Amaranth fast dissolving tablet containing Methanol extract of Amaranth dried leaves (8.25 mg nitrate per tablet) (Tablet prepared as per example No. 22 and extract used for preparing the tablet is as per example 3).

Group 5: Amaranth fast dissolving tablet containing water extract of Amaranth fresh leaves (8 mg nitrate per tablet) (Tablet prepared as per example No 22 and extract used for preparing the tablet is as per example 2).

Group 6: Amaranth fast dissolving tablet containing water extract of Amaranth dried leaves (8.5 mg nitrate per tablet) (Tablet prepared as per example No 22 and extract used for preparing the tablet is as per example 4)

Group 7: Amaranth fast dissolving tablet containing Pectinase treated water extract of Amaranth fresh leaves (10 mg nitrate per tablet) (Tablet prepared as per example No 22 and extract used for preparing the tablet is as per example 5)

Group 8: Amaranth fast dissolving tablet containing amaranth nitrate enriched extract (90 mg nitrate per tablet) (Tablet prepared as per example No 22 and extract used for preparing the tablet is as per example 7)

All subjects were allowed to consume the water/Juice orally (Group No-1 to 2). Amaranth Tablet were kept in oral cavity and allow to dissolve (Group No-3 to 8)

After each of the time point 1 hour, 2 hour and 3 hour from feeding, saliva was collected from all subjects in 5.0 ml PTFE tubes. This saliva was stored below −80 degree Celsius until analysis for $NO_3$ and $NO_2$ content. The saliva thus obtained was deprotenized using Acetonitrile and the supernatant liquid was used for $NO_3$ and $NO_2$ determination using HPLC. $NO_3$ was analyzed by HPLC on a BETASIL C-18 column (250×4.6 mm) using Tetra butyl ammonium hydroxide in De-ionized water, acetonitrile and methanol as mobile phase and Photo diode array detection at 222 nm. $NO_2$ was analyzed at 520 nm using the same conditions. The Nitrate and Nitrite of the saliva are reported as µmol/L.

TABLE

Nitrate (NO$_3$) content in saliva

| SI NO | Groups | Base line NO$_3$ levels (μmol/l) | NO$_3$ levels after 1 hour (μmol/l) | NO$_3$ levels after 2 hour (μmol/l) | NO$_3$ levels after 3 hour (μmol/l) |
|---|---|---|---|---|---|
| 1. | Vehicle Control | 292.54 | 295.66 | 295.95 | 290.57 |
| 2. | Amaranth fresh juice as such | 295.56 | 298.25 | 297.20 | 295.57 |
| 3. | Amaranth fast dissolving tablet containing methanol extract of fresh leaves | 296.55 | 299.35 | 299.10 | 297.01 |
| 4. | Amaranth fast dissolving tablet containing water extract of fresh leaves | 298.82 | 302.72 | 300.2 | 299.84 |
| 5. | Amaranth fast dissolving tablet containing methanol extract of dried leaves | 295.02 | 299.06 | 298.35 | 296.77 |
| 6. | Amaranth fast dissolving tablet containing water extract of dried leaves | 298.25 | 302.35 | 301.5 | 299.56 |
| 7. | Amaranth fast dissolving tablet containing pectinase treated water extract of fresh leaves | 296.50 | 300.78 | 298.8 | 297.23 |
| 8. | Amaranth fast dissolving tablet containing enriched extract of nitrate | 297.80 | 2062.25 | 2120.2 | 1895.51 |

TABLE

Nitrite (NO$_2$) content in saliva

| SI NO | Groups | Base line NO$_2$ levels (μmol/l) | NO$_2$ levels after 1 hour (μmol/l) | NO$_2$ levels after 2 hour (μmol/l) | NO$_2$ levels after 3 hour (μmol/l) |
|---|---|---|---|---|---|
| 1. | Vehicle Control | 112.54 | 113.55 | 112.95 | 115.39 |
| 2. | Amaranth fresh juice as such | 115.26 | 122.57 | 120.68 | 116.56 |
| 3. | Amaranth fast dissolving tablet containing methanol extract of fresh leaves | 113.50 | 121.00 | 120.65 | 119.82 |
| 4. | Amaranth fast dissolving tablet containing water extract of fresh leaves | 118.82 | 126.42 | 124.66 | 118.56 |
| 5. | Amaranth fast dissolving tablet containing methanol extract of dried leaves. | 114.93 | 122.63 | 120.44 | 119.64 |
| 6. | Amaranth fast dissolving tablet containing water extract of dried leaves | 115.65 | 123.45 | 120.23 | 117.38 |
| 7. | Amaranth fast dissolving tablet containing pectinase treated water extract of fresh leaves | 118.56 | 126.46 | 125.56 | 120.25 |
| 8. | Amaranth fast dissolving tablet containing enriched extract of nitrate | 115.78 | 1075.20 | 1005.20 | 782.50 |

TABLE

Total nitric oxide (NO) content in saliva

| SI NO | Groups | Base line NO levels (μmol/l) | NO levels after 1 hour (μmol/l) | NO levels after 2 hour (μmol/l) | NO levels after 3 hour (μmol/l) |
|---|---|---|---|---|---|
| 1. | Vehicle Control | 405.08 | 409.21 | 408.9 | 405.96 |
| 2. | Amaranth fresh juice as such | 410.82 | 420.82 | 417.88 | 412.13 |

TABLE-continued

Total nitric oxide (NO)content in saliva

| SI NO | Groups | Base line NO levels (μmol/l) | NO levels after 1 hour (μmol/l) | NO levels after 2 hour (μmol/l) | NO levels after 3 hour (μmol/l) |
|---|---|---|---|---|---|
| 3. | Amaranth fast dissolving tablet containing methanol extract of fresh leaves | 410.05 | 420.35 | 419.75 | 416.83 |
| 4. | Amaranth fast dissolving tablet containing water extract of fresh leaves | 417.64 | 429.14 | 424.86 | 418.80 |
| 5. | Amaranth fast dissolving tablet containing methanol extract of dried leaves. | 409.95 | 421.69 | 418.79 | 416.41 |
| 6. | Amaranth fast dissolving tablet containing water extract of dried leaves | 413.90 | 425.80 | 421.73 | 416.94 |
| 7. | Amaranth fast dissolving tablet containing pectinase treated water extract of fresh leaves | 415.06 | 427.24 | 424.36 | 417.48 |
| 8. | Amaranth fast dissolving tablet containing enriched extract of nitrate | 413.58 | 3137.45 | 3125.40 | 2678.01 |

Amaranth fresh juice consumption as such slightly increased the $NO_3$ content after one hour. Methanol extract from amaranth fresh leaves and dried leaves also showed a slight increase in $NO_3$ content. Tablet made with pectinase treated water extract of fresh leaves of Amaranth shown a little more increase than the other tablets consumptions. But after consumption of fast dissolving tablet containing Amaranth extract enriched with nitrate, $NO_3$ level increased to 6.9 fold the baseline value after 1 hour and the increase in $NO_3$ was maintained for 3 hours. There was no significant change in $NO_3$ level after administering the vehicle.

In case of $NO_2$ also, the fast dissolving tablet containing Amaranth extract enriched with nitrate, increased the $NO_2$ level more than 9.2 fold and the increase in $NO_2$ was maintained for 3 hours. Amaranth fresh juice consumption as such slightly increased the $NO_2$ content after one hour. Methanol extract from amaranth fresh leaves and dried leaves also showed a slight increase in $NO_2$ content. Here also vehicle did not influenced $NO_2$ level in the subjects.

Overall conclusion is that the total $NO_3$ and $NO_2$ level increase was observed in Amaranth fast dissolving tablet was more compared with—Amaranth fresh juice, Methanol extract from fresh and dried leaves. The increase in total NO content of "Amaranth fast dissolving tablet containing enriched extract of nitrate" is 7.5 fold from base line and it remained increased for 3 hours. Total NO was interpreted as the sum of total $NO_3$ and $NO_2$. Level of $NO_3$ and $NO_2$ was used to interpret the level of NO level in human body. So an increase in $NO_3$ and $NO_2$ level was interpreted as an increase in NO level. NO levels was recorded as the sum of the two major metabolites of NO, namely, nitrite and nitrate. (Journal of Medical sciences (2010):3 (3): 153-159, Plasma Endothelin—1, Homocysteine, and Oxide Levels in a Multiethnic Hypertensive Cohort from the United Arab Emirates.)

EXAMPLE 34

Nitrate ($NO_3$) Nitrite ($NO_2$) and Nitric Oxide (NO) Content in Saliva of Human Subjects 18 Healthy human volunteers (age 35-55 years) were taken for the study. The subjects were put on controlled diet, one week prior to the study. The subjects were divided into three groups comprising of six subjects in each group. The subjects were fasted overnight and saliva was collected to determine the base line $NO_3$ and $NO_2$ levels. After saliva collection, the subjects were treated as follows:

Group 1: Vehicle control. (Water)

Group 2: Amaranth leaves fresh juice as such—100 ml (100 mg Nitrate/100 ml of juice) (Prepared as per example No-13)

Group 3: Amaranth extract with enriched nitrate (18% nitrate prepared as per example 7) is mixed with water. (560 mg of extract in 300 ml water)

All subjects were allowed to consume the water/Juice orally (Group No-1 to 2). Amaranth extract enriched with nitrate mixed with water was consumed directly in the oral cavity (Group No-3)

After each of the time point 1 hour, 2 hour and 3 hour from feeding, saliva was collected from all subjects in 5.0 ml PTFE tubes. This saliva was stored below −80 degree Celsius until analysis for $NO_3$ and $NO_2$ content. The saliva thus obtained was deprotenized using Acetonitrile and the supernatant liquid was used for $NO_3$ and $NO_2$ determination using HPLC. $NO_3$ was analyzed by HPLC on a BETASIL C-18 column (250×4.6 mm) using Tetra butyl ammonium hydroxide in De-ionized water, acetonitrile and methanol as mobile phase and Photo diode array detection at 222 nm. $NO_2$ was analyzed at 520 nm using the same conditions. The Nitrate and Nitrite of the saliva were reported as μmol/L.

TABLE

Nitrate (NO$_3$) content in saliva

| SI NO | Groups | Base line NO$_3$ levels (μmol/l) | NO$_3$ levels after 1 hour (μmol/l) | NO$_3$ levels after 2 hour (μmol/l) | NO$_3$ levels after 3 hour (μmol/l) |
|---|---|---|---|---|---|
| 1. | Vehicle Control | 295.65 | 296.55 | 293.78 | 296.58 |
| 2. | Amaranth fresh juice as such | 296.23 | 300.02 | 297.02 | 296.33 |
| 3. | Amaranth extract with enriched nitrate mixed with water | 295.68 | 1961.51 | 1901.27 | 789.56 |

TABLE

Nitrite (NO$_2$) content in saliva

| SI NO | Groups | Base line NO$_2$ levels (μmol/l) | NO$_2$ levels after 1 hour (μmol/l) | NO$_2$ levels after 2 hour (μmol/l) | NO$_2$ levels after 3 hour (μmol/l) |
|---|---|---|---|---|---|
| 1. | Vehicle Control | 110.56 | 112.56 | 110.94 | 113.24 |
| 2. | Amaranth fresh juice as such | 113.54 | 120.56 | 119.85 | 113.55 |
| 3. | Amaranth extract with enriched nitrate mixed with water | 115.60 | 1060.45 | 1055.33 | 814.34 |

TABLE

Total nitric oxide (NO) content in Saliva

| SI NO | Groups | Base line NO levels (μmol/l) | NO levels after 1 hour (μmol/l) | NO levels after 2 hour (μmol/l) | NO levels after 3 hour (μmol/l) |
|---|---|---|---|---|---|
| 1. | Vehicle Control | 406.21 | 409.11 | 404.72 | 409.82 |
| 2. | Amaranth fresh juice as such | 409.77 | 420.58 | 416.87 | 409.88 |
| 3. | Amaranth extract with enriched nitrate mixed with water | 411.28 | 3021.96 | 2956.60 | 1603.90 |

Amaranth fresh juice consumption as such slightly increased the NO$_3$ content after one hour. But after consumption of Amaranth extract with enriched nitrate mixed with water, NO$_3$ level increased to 6.6 fold the baseline value after 1 hour and remained increased for 3 hours. There was no significant change in NO$_3$ level after administering the vehicle.

In case of NO$_2$ also, Amaranth extract with enriched nitrate mixed with water increased the NO$_2$ level 9.1 fold and remained increased for 3 hours. Amaranth fresh juice consumption as such slightly increased the NO$_2$ content after one hour.

Overall conclusion is that the total NO$_3$ and NO$_2$ level increase observed by administering Amaranth enriched extract mixed with water was more when compared with administering Amaranth fresh juice. The increase in total NO content of "Amaranth enriched extract mixed with water" was 7.3 times from baseline and it remained increased for 3 hours.

EXAMPLE 35

Nitrate (NO$_3$), Nitrite (NO$_2$) and Nitric Oxide (NO) Content in Plasma and Saliva of Human Subjects After Administering Extract of *Amaranthus Blitum* and *Amaranthus Viridus* with Enriched Nitrate.

Nine healthy human volunteers (age 35-55 years) were taken for the study. The subjects were put on standard diet one week prior to the study. The subjects were divided into three groups comprising of three subjects in each group. The subjects were fasted overnight and the blood and saliva was collected to determine the baseline NO$_3$ and NO$_2$ levels. After baseline blood and saliva collection, the subjects were treated as follows:

Group 1: Vehicle Control.

Group 2: Amaranth fast dissolving tablet containing extract of *Amaranthus blitum* with enriched nitrate (91.5 mg nitrate per tablet) (Tablet prepared as per example No 22 and extract used for preparing the tablet is as per example 15).

Group 3: Amaranth fast dissolving tablet containing extract of *Amaranthus viridus* with enriched nitrate (90.5 mg nitrate per tablet) (Tablet prepared as per example No 22 and extract used for preparing the tablet is as per example 15).

All subjects were allowed to consume the water orally (Group No. 1). Amaranth Tablets were kept in oral cavity and allow to dissolve (Group No. 2 to 3).

After 1 hour, 2 hour and 3 hour from feeding of tablet/vehicle, blood was drawn from all the subjects in EDTA coated tubes and saliva was collected from the same subjects in 5.0 ml PTFE tubes. Plasma was separated immediately by centrifuging the tubes at 5000 rpm for 15 min. The plasma samples and saliva were stored below −80 degree Celsius until analysis. The plasma and saliva were deproteinized using Acetonitrile and the supernatant liquid was used for nitrate/nitrite determination using HPLC. $NO_3$ was analyzed by HPLC on a BETASIL C-18 column (250×4.6 mm) using Tetra butyl ammonium hydroxide in De-ionized water, acetonitrile and methanol as mobile phase and photo diode array detection at 222 nm. $NO_2$ was analysed at 520 nm using the same conditions. The $NO_3$ and $NO_2$ levels in plasma were reported as μmol/L.

Nitrate ($NO_3$), Nitrite ($NO_2$) and Nitric Oxide (NO) Level in Plasma

TABLE

| | | Nitrate ($NO_3$) content in plasma | | | |
|---|---|---|---|---|---|
| SI NO | Groups | Baseline $NO_3$ levels (μmol/l) | $NO_3$ levels after 1 hour (μmol/l) | $NO_3$ levels after 2 hour (μmol/l) | $NO_3$ levels after 3 hour (μmol/l) |
| 1. | Vehicle Control | 28.92 | 28.95 | 27.88 | 28.81 |
| 2. | Fast dissolving tablet containing extract of *Amaranthus blitum* with enriched nitrate. | 28.41 | 172.50 | 109.43 | 70.5 |
| 3. | Fast dissolving tablet containing extract of *Amaranthus viridus* with enriched nitrate. | 27.65 | 168.92 | 110.22 | 70.89 |

TABLE

| | | Nitrite ($NO_2$) content in plasma | | | |
|---|---|---|---|---|---|
| SI No | Groups | Base line $NO_2$ levels (μmol/l) | $NO_2$ levels after 1 hour (μmol/l) | $NO_2$ levels after 2 hour (μmol/l) | $NO_2$ levels after 3 hour (μmol/l) |
| 1. | Vehicle Control | 0.19 | 0.20 | 0.23 | 0.18 |
| 2. | Fast dissolving tablet containing extract of *Amaranthus blitum* with enriched nitrate. | 0.19 | 1.15 | 0.94 | 0.59 |
| 3. | Fast dissolving tablet containing extract of *Amaranthus viridus* with enriched nitrate. | 0.21 | 1.27 | 0.97 | 0.65 |

TABLE

| | | Total nitric oxide (NO) content in plasma | | | |
|---|---|---|---|---|---|
| SI NO | Groups | Base line NO levels (μmol/l) | NO levels after 1 hour (μmol/l) | NO levels after 2 hour (μmol/l) | NO levels after 3 hour (μmol/l) |
| 1. | Vehicle Control | 29.11 | 29.15 | 28.11 | 28.99 |
| 2. | Fast dissolving tablet containing extract of *Amaranthus blitum* with enriched nitrate | 28.6 | 173.65 | 110.37 | 71.09 |
| 3. | Fast dissolving tablet containing extract of *Amaranthus viridus* with enriched nitrate. | 27.86 | 170.19 | 111.19 | 71.54 |

After consumption of fast dissolving tablet containing extract of *Amaranthus blitum* and *Amaranthus viridus* with enriched nitrate, $NO_3$ level increased to 6 fold the baseline value after 1 hour and the increase from base line was maintained up to 3 hour. There was no significant change in $NO_3$ level after administering the vehicle.

In case of $NO_2$ also, the fast dissolving tablet containing extract of *Amaranthus blitum* and *Amaranthus viridus* with enriched nitrate, increased the $NO_2$ level more than 6 times and the higher levels maintained for 3 hours. Here also vehicle did not influence $NO_2$ level in the subjects.

The increase in total nitric oxide (NO) content of "Amaranth fast dissolving tablet containing extract of *Amaranthus blitum* and *Amaranthus viridus* with enriched nitrate" was 6 times from base line and it remained increased for 3 hours. Total NO was determined from the sum of total $NO_3$ and $NO_2$. (i.e. Level of $NO_3$ and $NO_2$ can be interpreted as a measure of NO level in human body). So an increase in $NO_3$ and $NO_2$ level was interpreted as an increase in NO level.

Nitrate ($NO_3$), Nitrite ($NO_2$) and Nitric Oxide (NO) Level in Saliva

TABLE

| | | \multicolumn{4}{c}{Nitrate ($NO_3$) content in saliva} | | | |
|---|---|---|---|---|---|
| SI NO | Groups | Base line $NO_3$ levels (μmol/l) | $NO_3$ levels after 1 hour (μmol/l) | $NO_3$ levels after 2 hour (μmol/l) | $NO_3$ levels after 3 hour (μmol/l) |
| 1. | Vehicle Control | 292.54 | 295.66 | 295.95 | 290.57 |
| 2. | Fast dissolving tablet containing extract of *Amaranthus blitum* with enriched nitrate | 297.10 | 2058.9 | 2184.2 | 1796.51 |
| 3. | Fast dissolving tablet containing extract of *Amaranthus viridus* with enriched nitrate | 296.7 | 2047.52 | 2147.2 | 1801.12 |

TABLE

| | | \multicolumn{4}{c}{Nitrite ($NO_2$) content in saliva} | | | |
|---|---|---|---|---|---|
| SI NO | Groups | Base line $NO_2$ levels (μmol/l) | $NO_2$ levels after 1 hour (μmol/l) | $NO_2$ levels after 2 hour (μmol/l) | $NO_2$ levels after 3 hour (μmol/l) |
| 1 | Vehicle Control | 112.54 | 113.55 | 112.95 | 115.39 |
| 2 | Fast dissolving tablet containing extract of *Amaranthus blitum* with enriched nitrate | 115.75 | 1064.9 | 1021.1 | 796.70 |
| 3 | Fast dissolving tablet containing extract of *Amaranthus viridus* with enriched nitrate | 113.58 | 1033.57 | 1001.4 | 701.3 |

TABLE

| | | \multicolumn{4}{c}{Total nitric oxide (NO) content in saliva} | | | |
|---|---|---|---|---|---|
| SI NO | Groups | Base line NO levels (μmol/l) | NO levels after 1 hour (μmol/l) | NO levels after 2 hour (μmol/l) | NO levels after 3 hour (μmol/l) |
| 1. | Vehicle Control | 405.08 | 409.21 | 408.9 | 405.96 |
| 2. | Fast dissolving tablet containing extract of *Amaranthus blitum* with enriched nitrate | 412.85 | 3123.8 | 3205.3 | 2593.21 |
| 3. | Fast dissolving tablet containing extract of *Amaranthus viridus* with enriched nitrate | 410.28 | 3081.09 | 3148.6 | 2502.42 |

After consumption of fast dissolving tablet containing extract of *Amaranthus blitum* and *Amaranthus viridus* with enriched nitrate, $NO_3$ level increased to 6.9 fold the baseline value after 1 hour and the increase in $NO_3$ was maintained for 3 hours. There was no significant change in $NO_3$ level after administering the vehicle.

In case of $NO_2$ also, the fast dissolving tablet containing extract of *Amaranthus blitum* and *Amaranthus viridus* with enriched nitrate, increased the $NO_2$ level more than 9.2 fold and the increase in $NO_2$ was maintained for 3 hours. Here also vehicle did not influenced $NO_2$ level in the subjects.

The increase in total NO content of "Amaranth fast dissolving tablet containing extract of *Amaranthus blitum* and *Amaranthus viridus* with enriched nitrate" was 7.5 fold from base line and it remained increased for 3 hours. Total NO was interpreted as the sum of total $NO_3$ and $NO_2$. (Level of $NO_3$ and $NO_2$ is used to interpret the level of NO level in human body). So an increase in $NO_3$ and $NO_2$ level was interpreted as an increase in NO level.

It will be readily understood by the skilled artisan that numerous alterations may be made to the examples and instructions given herein. These and other objects and features of disclosed embodiments will be made apparent from the following examples. The following examples as described are not intended to be construed as limiting the scope of the disclosure.

I claim:

1. A tablet or capsule for lowering blood pressure in a human in need thereof consisting essentially of therapeutically effective amounts of amla extract, Amaranth extract, green tea extract, pomegranate extract, turmeric extract and star anise extract.

2. A tablet or capsule for increasing physical endurance in a human in need thereof consisting essentially of therapeutically effective amounts of amla extract, Amaranth extract, green tea extract, pomegranate extract, turmeric extract and star anise extract.

3. A tablet or capsule for increasing swimming endurance in a human in need thereof consisting essentially of therapeutically effective amounts of amla extract, Amaranth extract, green tea extract, pomegranate extract, turmeric extract and star anise extract.

4. A tablet or capsule for increasing running endurance in a human in need thereof consisting essentially of therapeutically effective amounts of amla extract, Amaranth extract, green tea extract, pomegranate extract, turmeric extract and star anise extract.

* * * * *